United States Patent
Mitra et al.

(10) Patent No.: US 9,216,076 B2
(45) Date of Patent: *Dec. 22, 2015

(54) MEANS FOR CONTROLLED SEALING OF ENDOVASCULAR DEVICES

(75) Inventors: Ashish Sudhir Mitra, Sydney (AU); Martin Kean Chong Ng, Sydney (AU); Pak Man Victor Wong, Leichhardt (AU); Ben Colin Bobillier, Mosman (AU); Jens Sommer-Knudsen, East Killara (AU)

(73) Assignee: Endoluminal Sciences Pty. Ltd., Sydney (AU)

( * ) Notice: Subject to any disclaimer, the term of this patent is extended or adjusted under 35 U.S.C. 154(b) by 61 days.

This patent is subject to a terminal disclaimer.

(21) Appl. No.: 13/476,695

(22) Filed: May 21, 2012

(65) Prior Publication Data

US 2013/0197622 A1 Aug. 1, 2013

Related U.S. Application Data

(60) Provisional application No. 61/532,814, filed on Sep. 9, 2011.

(51) Int. Cl.
*A61F 2/06* (2013.01)
*A61L 31/14* (2006.01)
*A61F 2/07* (2013.01)
(Continued)

(52) U.S. Cl.
CPC ... *A61F 2/06* (2013.01); *A61F 2/07* (2013.01); *A61F 2/2409* (2013.01); *A61F 2/2418* (2013.01); *A61L 31/048* (2013.01); *A61L 31/06* (2013.01); *A61L 31/145* (2013.01); *A61L 31/16* (2013.01); *A61F 2/90* (2013.01);
(Continued)

(58) Field of Classification Search
CPC ............. A61B 17/1219; A61F 2002/072; A61F 2210/0061
See application file for complete search history.

(56) References Cited

U.S. PATENT DOCUMENTS 3,012,893 A 12/1961 Leon
5,769,882 A 6/1998 Fogarty
(Continued)

FOREIGN PATENT DOCUMENTS

WO 9851408 11/1998
WO 03089506 10/2003
(Continued)

OTHER PUBLICATIONS

Kim, et al., "Swelling and mechanical properties of superporous hydrogels of poly (acrylamide-co-acrylic acid)/polyethienimine interpenetrating polymer networks", Polymer, 45(1): 189-96 (2004).
(Continued)

*Primary Examiner* — Katherine M Shi
*Assistant Examiner* — Michael Mendoza
(74) *Attorney, Agent, or Firm* — Pabst Patent Group LLP

(57) ABSTRACT

Expandable sealing means for endoluminal devices have been developed for controlled activation. The devices have the benefits of a low profile mechanism (for both self-expanding and balloon-expanding prostheses), contained, not open, release of the material, active conformation to the "leak sites" such that leakage areas are filled without disrupting the physical and functional integrity of the prosthesis, and on-demand, controlled activation, that may not be pressure activated.

28 Claims, 12 Drawing Sheets

(51) Int. Cl.
*A61F 2/24* (2006.01)
*A61L 31/04* (2006.01)
*A61L 31/06* (2006.01)
*A61L 31/16* (2006.01)
*A61F 2/90* (2013.01)

(52) U.S. Cl.
CPC .. *A61F 2002/075* (2013.01); *A61F 2210/0061* (2013.01); *A61F 2220/005* (2013.01); *A61F 2250/0069* (2013.01)

(56) References Cited

U.S. PATENT DOCUMENTS

| | | | |
|---|---|---|---|
| 6,123,723 A * | 9/2000 | Konya et al. | 623/1.11 |
| 6,271,278 B1 | 8/2001 | Park | |
| 6,398,758 B1 * | 6/2002 | Jacobsen et al. | 604/104 |
| 2003/0204249 A1 | 10/2003 | Letort | |
| 2003/0232895 A1 | 12/2003 | Omidian | |
| 2004/0260382 A1 | 12/2004 | Fogarty | |
| 2007/0060998 A1 | 3/2007 | Butterwick | |
| 2007/0179600 A1 | 8/2007 | Vardi | |
| 2007/0244544 A1 * | 10/2007 | Birdsall et al. | 623/1.26 |
| 2008/0038325 A1 * | 2/2008 | Nho et al. | 424/443 |
| 2009/0099653 A1 | 4/2009 | Suri | |
| 2013/0138068 A1 * | 5/2013 | Hu et al. | 604/368 |

FOREIGN PATENT DOCUMENTS

| | | |
|---|---|---|
| WO | 2007121072 | 10/2007 |
| WO | 2008023160 | 2/2008 |
| WO | 2008042093 | 4/2008 |
| WO | 2010083558 | 7/2010 |

OTHER PUBLICATIONS

Qiu, et asl., "Superporous IPN hydrogels having enhanced mechanical properties", AAPS Pharm Sci Tech., 40(4):406-12 (2003).

Shazly, et al., "Augmentation of postswelling surgical sealant potential of adhesive hydrogels", J Biomed. Mat. Res., Pt A, 95A(4):1159-69 (2010).

* cited by examiner

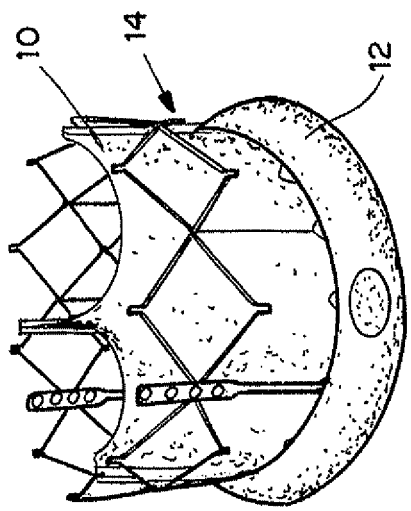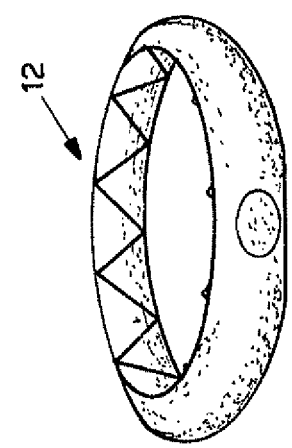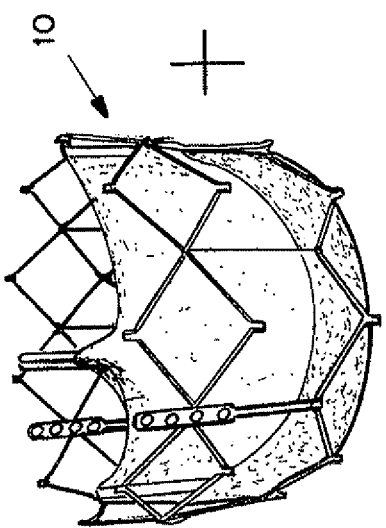

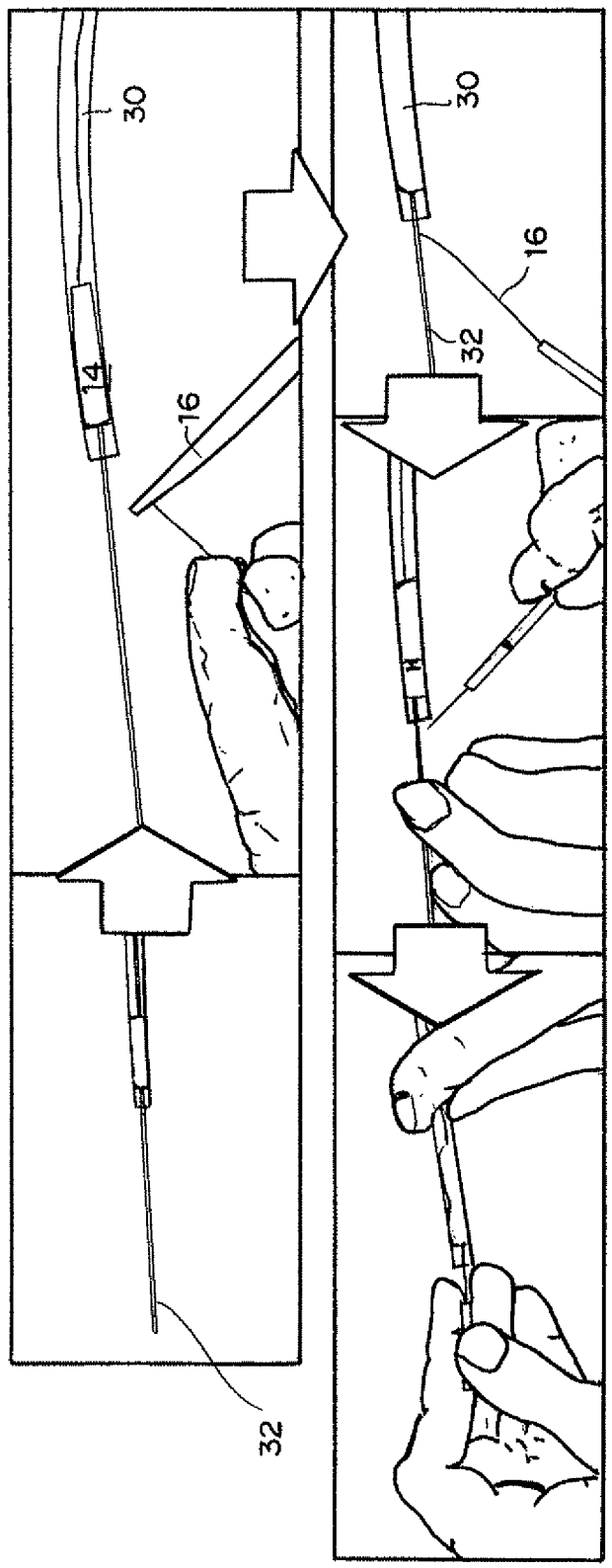

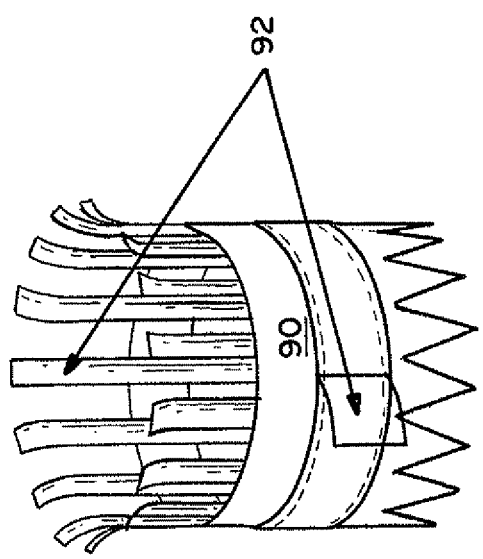
FIG. 7A
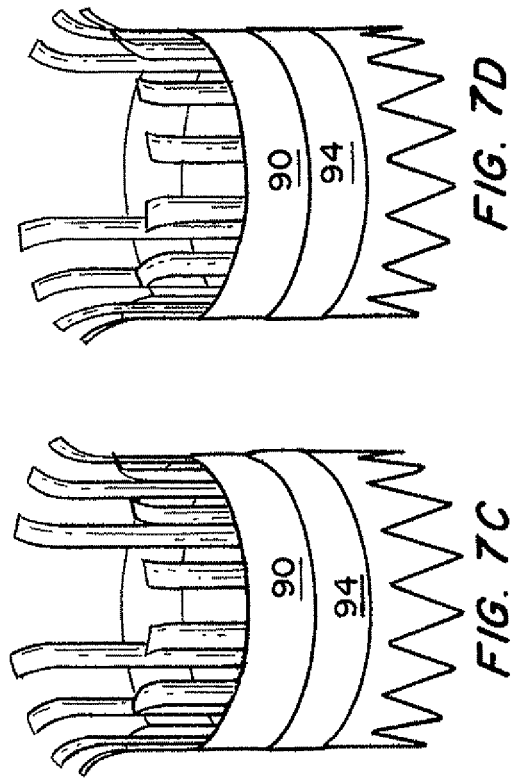
FIG. 7D
FIG. 7C
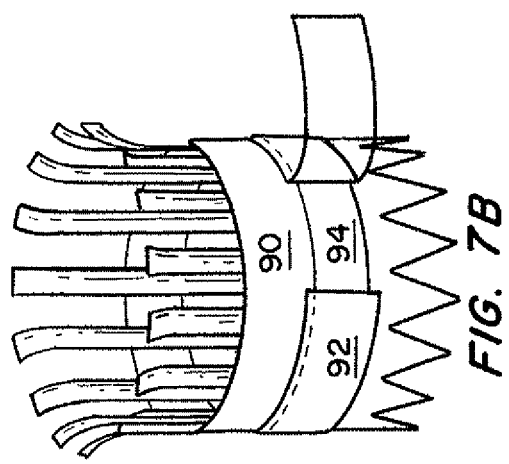
FIG. 7B

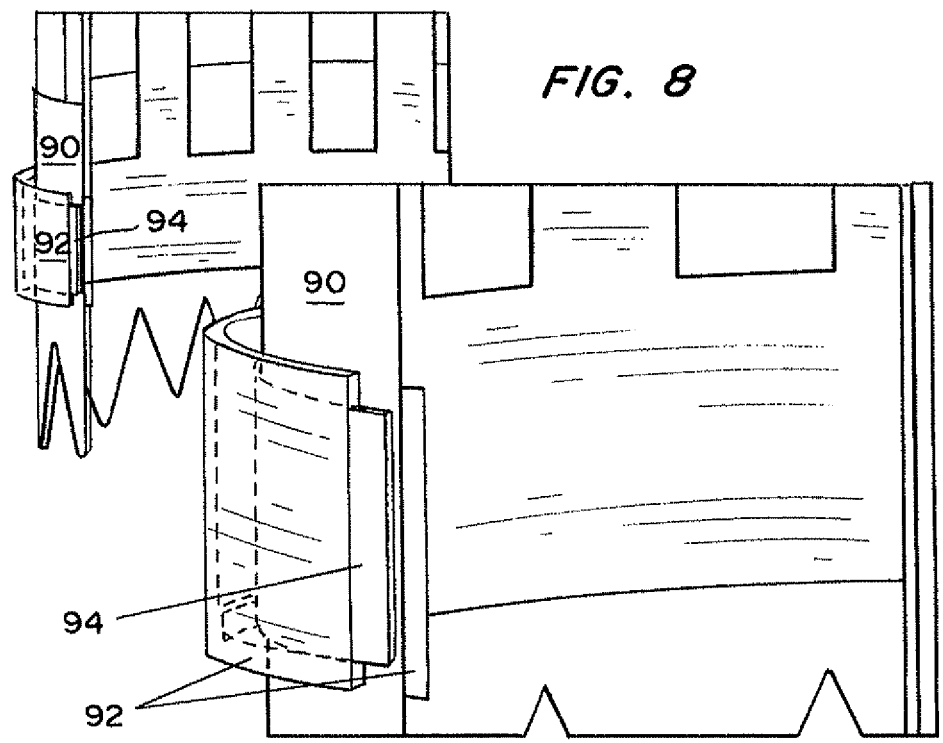

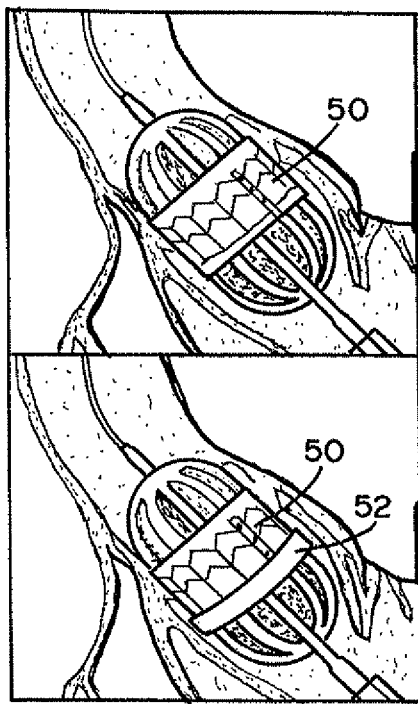
FIG. 9A
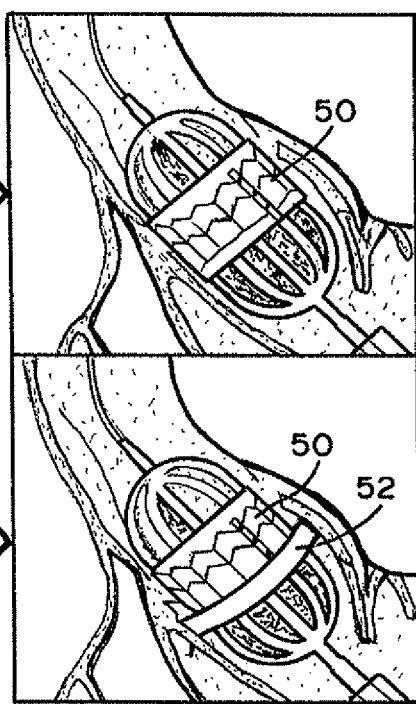
FIG. 9B
FIG. 9C
FIG. 9D
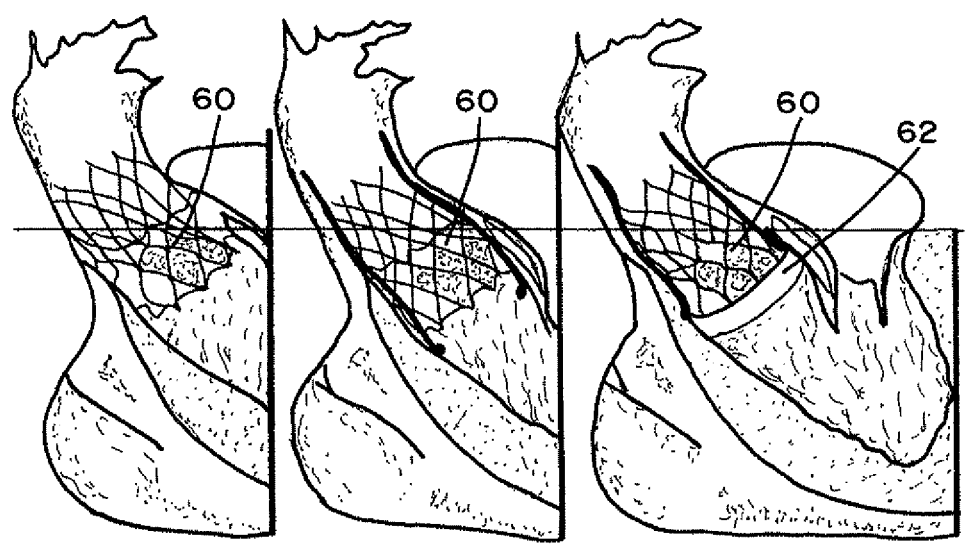
FIG. 10A  FIG. 10B  FIG. 10C

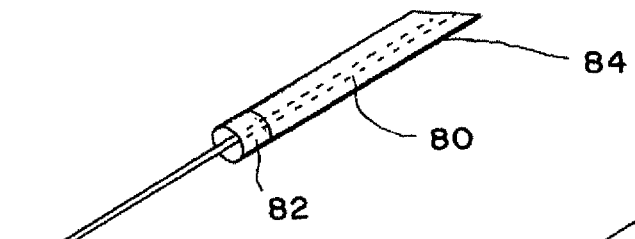
FIG. 11A
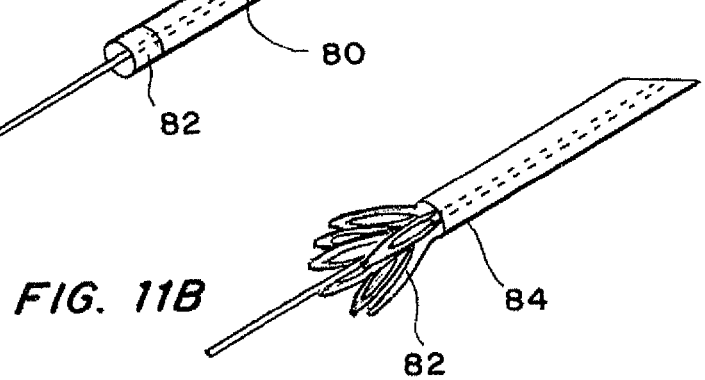
FIG. 11B
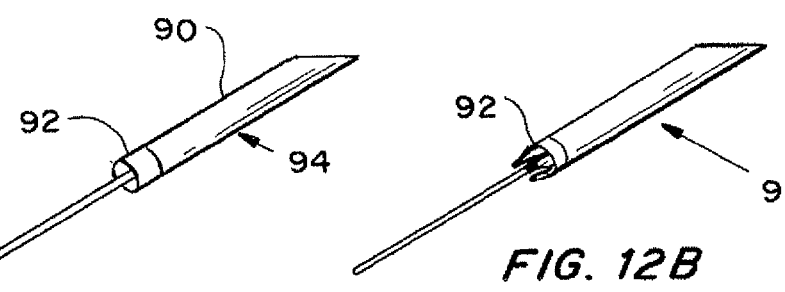
FIG. 12A
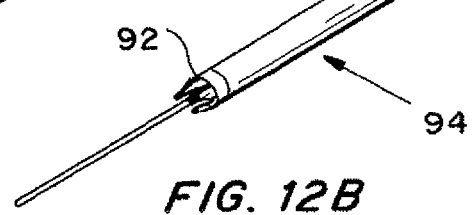
FIG. 12B
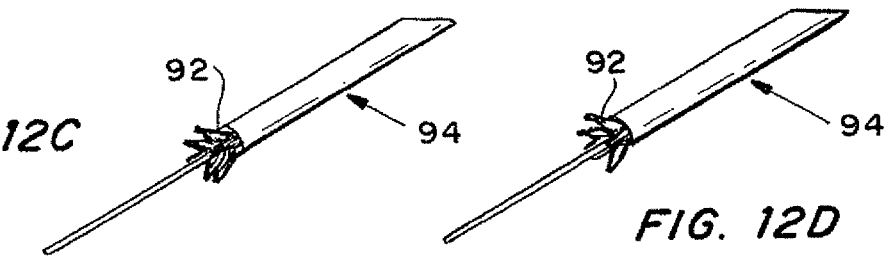
FIG. 12C
FIG. 12D
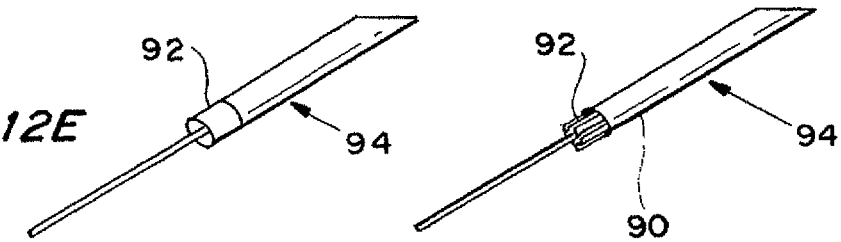
FIG. 12E
FIG. 12F ✷ GEL 29　▲ GEL 23　✕ GEL 24　○ GEL 26
− GEL 21 E　− GEL 17　◇ GEL 18　■ GEL 19
□ GEL 2　△ GEL 3　✳ GEL 5　✶ GEL 6　+ GEL 21 G

MEANS FOR CONTROLLED SEALING OF ENDOVASCULAR DEVICES

PRIOR RELATED APPLICATIONS

The present application claims the benefit of priority to U.S. Ser. No. 61/532,814 "Means for Controlled Sealing of Endovascular Devices" filed in the United States Patent and Trademark Office on Sep. 9, 2011, which is incorporated herein by reference in its entirety.

FIELD OF THE INVENTION

The present disclosure is directed generally to endoluminal devices and associated systems and methods, and specifically to a method and devices for controlled actuation of means for sealing of an endoluminal prosthesis to a vessel wall.

BACKGROUND OF THE INVENTION

An aneurysm is a localized, blood-filled dilation of a blood vessel caused by disease or weakening of the vessel wall. Aneurysms affect the ability of the vessel to conduct fluids, and can be life threatening if left untreated. Aneurysms most commonly occur in arteries at the base of the brain and in the aorta. As the size of an aneurysm increases, there is an increased risk of rupture, which can result in severe hemorrhage or other complications including sudden death.

Aneurysms are typically treated by surgically removing a part or all of the aneurysm and implanting a replacement prosthetic section into the body lumen. Such procedures, however, can require extensive surgery and recovery time. Patients often remain hospitalized for several days following the procedure, and can require several months of recovery time. Moreover, the morbidity and mortality rates associated with such major surgery can be significantly high.

Another approach for treating aneurysms involves deployment of an endovascular graft assembly at the affected site. Such procedures typically include intravascular delivery of the endovascular graft assembly to the site of the aneurysm. The graft is then expanded or deployed in situ and the ends of the graft are anchored to the body lumen on each side of the aneurysm. In this way, the graft effectively excludes the aneurysm sac from circulation.

One concern with many conventional endovascular graft assemblies, however, is the long term durability of such structures. Over time, for example, the graft can become separated from an inner surface of the body lumen, and such separation can result in endoleaks. As used herein, endoleak is defined as a persistent blood or other fluid flow outside the lumen of the endoluminal graft, but within the aneurysm sac or adjacent vascular segment being treated by the device. When an endoleak occurs, it can cause continuous pressurization of the aneurysm sac and may result in an increased risk of rupture.

In addition to endoleaks, another concern with many conventional endovascular graft assemblies is the delivery of endoluminal reactants to such devices. For example, after a surgeon has found an optimal location for the graft, the device must be fixed to the wall of the body lumen and fully sealed at each end of the graft to prevent endoleaks and achieve a degree of fixation that will prevent subsequent device migration and/or dislodgement.

Aortic stenosis, also known as aortic valve stenosis, is a sinister disease characterized by an abnormal narrowing of the aortic valve. The narrowing prevents the valve from opening fully, which obstructs blood flow from the heart into the aorta. As a result, the left ventricle has to work harder to maintain adequate blood flow through the body. If left untreated, aortic stenosis can lead to life-threatening problems including heart failure, irregular heart rhythms, cardiac arrest, and chest pain.

Aortic stenosis is typically due to age-related progressive calcification of the normal trileaflet valve, though other predisposing conditions include congenital heart defects, calcification of a congenital bicuspid aortic valve, and acute rheumatic fever. Conditions including hypertension, diabetes mellitus, hyperlipoproteinemia and uremia may speed up the process. Aortic stenosis is characterized by a long latency period followed by rapid progression after the appearance of symptoms, resulting in a high rate of death (approximately 50% in the first 2 years after symptoms appear) among untreated patients. Typically, aortic stenosis due to calcification of a bicuspid valve manifests when individuals reach their 40s and 50s, whereas symptoms due to calcification of a normal valve more commonly appear in the 70s and 80s.

For the last fifty years open heart surgery for aortic valve replacement with use of cardiopulmonary bypass, sternotomy (or mini-sternotomy), aortic cross clamping and cardioplegic arrest represents the treatment of choice and the standard of care for patients carrying severe aortic stenosis with symptoms (Borrow, et al., *Circulation*, 114:e84-231 (2006), Kvidal, et al., *J. Am. Coll. Cardiol.*, 35:747-56 (2000), Otto, *Heart*, 84:211-8 (2000), Schwarz, et al., *Circulation*, 66:110510 (1982)). However, because the disease most often occurs in the elderly (a prevalence of 4.6% in adults aged 75 years or more), there is still a large pool of patients affected by severe aortic stenosis (estimated at 33% of patients with severe symptomatic aortic stenosis) who are not candidates for open heart valve replacement surgery because they are considered too old (nonagenarians, centenaries) for such an invasive procedure, or because they are also affected by other co-existing conditions that compound their operative risk (Jung, et al., *Eur Heart J.* 26:2714-20 (2005). For these patients, who are at high surgical risk, a less invasive treatment is necessary.

Transcatheter aortic-valve implantation (TAV) is a procedure in which a bioprosthetic valve is inserted through a catheter and implanted within the diseased native aortic valve. The most common implantation routes include the transapical approach (TA) and transfermoral (TF), though trans-subclavian and trans-aortic routes are also being explored (Ferrari, et al., *Swiss Med Wkly*, 140:w13127 (2010). These percutaneous routes rely on a needle catheter getting access to a blood vessel, followed by the introduction of a guidewire through the lumen of the needle. It is over this wire that other catheters can be placed into the blood vessel, and implantation of the prosthesis is carried out. During TAV procedures, regardless of the implantation route utilized, the guidewire must traverse the aortic arch to sustain delivery of the prosthesis to the site of the native aortic valve.

Since 2002 when the procedure was first performed, there has been rapid growth in its use throughout the world for the treatment of severe aortic stenosis in patients who are at high surgical risk, and there is mounting support to adopt the therapy as the standard of care for patients that are not at a high risk for surgery. Clinical studies have shown that the rate of death from any cause at the one-year mark among patients treated with TAV was approximately 25% (Grube, et al., *Circ. Cardiovasc. Interv.* 1:167-175 (2008), Himbert et al., *J. Am. Coll. Cardia*, 54:303-311 (2009), Webb, et al., *Circulation*, 119:3009-3016 (2009), Rodes-Cabau, et al., *J. Am. Coll. Cardiol.*, 55:1080-1090 (2010), and the results of two parallel prospective, multicenter, randomized, active-treatment-controlled clinical trials showed that TAV is superior to standard therapy, when comparing the rate of death from any cause at the 1-year mark (30.7% in the TAV group, as compared with 50.7% in the standard-therapy group) (Leon, et al., *N. Engl. J. Med.*, 363:1597-1607 (2010)).

Paravalvular leaks are extremely rare in surgical aortic-valve replacement—seen in just 1.5% to 2% of cases. But as experts observed at *Euro PCR* 2011, mild paravalvular leaks are relatively common in transcatheter aortic-valve implantation (TAV), and new data suggest that more severe paravalvular aortic regurgitation (AR) is a key reason for prosthetic valve dysfunction. According to Dr Jan-Matte Sinning (Universitatsklinikum, Bonn, Germany), moderate to severe periprosthetic aortic regurgitation occurs in approximately 15% of TAV-treated patients, a number drawn from 12 international registries. In 127 consecutive patients treated with TAV at his center, 21 developed moderate paravalvular AR postprocedure, and this was associated with a significantly higher rate of 30-day and one-year mortality, as well as acute kidney injury, compared with patients with no or mild AR. Predictors of paravalvular AR included a low baseline left ventricular ejection fraction (LVEF) and inadequate sizing of the annulus or device. Dr Kensuke Takagi (San Raffaele Hospital, Milan, Italy), reported that at his center, 32 patients developed AR grade 2+ to 4+, out of 79 consecutive patients treated with the CoreValve (Medtronic). In multivariate analyses, valve-annulus mismatch, particularly in larger aortic annuli, was a significant predictor of developing more severe paravalvular AR; an even stronger predictor was low implantation of the valve, which increased the risk by more than threefold. And while postdilatation can help treat paravalvular AR, this is appropriate only in patients in whom the valve was correctly positioned at the outset, Takagi said.

The Valve Academic Research Consortium criteria makes it possible, for the first time, for centers to assess their paravalvular leaks against a standardized definition. See Leon M B, Piazza N, Nikolsky E, et al. Standardized endpoint definitions for transcatheter aortic valve implantation clinical trials. *J Am Coll Cardiol* 2011; 57:253-269; *Eur Heart J* 2011; 32:205-217

The major potential offered by solving leaks with transcatheter heart valves is in growing the market to the low risk patient segment. The market opportunity in the low-risk market segment is double the size of that in the high risk segment and therefore it is imperative for a TAV device to have technology to provide superior long-term hemodynamic performance so that the physicians recommend TAV over SAVR.

More than 3 million people in the United States suffer from moderate or severe mitral regurgitation (MR), with more than 250,000 new patients diagnosed each year. Functional MR can be found in 84% of patients with congestive heart failure and in 65% of them the degree of regurgitation is moderate or severe. The long term prognostic implications of functional mitral regurgitation have demonstrated a significant increase in risk for heart failure or death, which is directly related to the severity of the regurgitation. Compared to mild regurgitation, moderate to severe regurgitation was associated with a 2.7 fold risk of death and 3.2 fold risk of heart failure, and thus significantly higher health care cost. Treatment of mitral valve regurgitation depends on the severity and progression of signs and symptoms. Left unchecked, mitral regurgitation can lead to heart enlargement, heart failure and further progression of the severity of mitral regurgitation. For mild cases, medical treatment may be sufficient. For more severe cases, heart surgery might be needed to repair or replace the valve.

Currently, these are open-chest/open-heart procedures that carry significant risk, especially for elderly patients and those with severe co-morbidities. Millions suffer from MR worldwide, yet only about 80,000 surgical repair or replacement procedures are performed each year. This significant treatment gap is largely due to the risk associated with the currently available surgeries. The development of less-invasive alternatives to surgical treatment options addresses a substantial unmet clinical need. While several companies are attempting to develop less invasive approaches to repair the mitral valve, they have found limited anatomical applicability due to the heterogeneous nature of the disease and, so far, have had a difficult time demonstrating efficacy that is equivalent to surgical approaches. Innovative approaches to less invasive heart valve replacement are a promising alternative and Transcatheter Mitral Valve Implantation (TMVI) devices are under development. PVL is likely to be a major problem with these devices and more critical than it is in the case of TAV devices. TAV and TMVI devices may also be used to treat the disease states of aortic insufficiency (or aortic regurgitation) and mitral stenosis respectively, which are less prevalent compared to the aforementioned valvular disease states yet have similar or worse clinical prognosis/severity. They can also be implanted within failing bioprostheses that are already implanted surgically, which is termed as a valve-in-valve procedure.

An improved device for treatment of these conditions has been developed which includes a means for sealing the device at the site of placement, using a sealing ring that is activated by pressure as it is expanded in situ. As the device expands, a swellable material is released into the sealing means that causes the sealing means to expand and conform to the vessel walls, securing it in place. See WO2010/083558 by Endoluminal Sciences Pty Ltd. Occasionally, however, the sealing means does not activate at the most desired point within the vasculature or application of pressure may be undesirable.

It is therefore an object of the present invention to provide physician controllable means for sealing endovascular devices such as stents and aortic valves in situ.

It is a further object of the present invention to provide stents and aortic valves having sealing means attached thereto for activation by a physician implanting the devices.

It is a further object of the present invention to allow for active conformation of the sealing means to the vascular anatomy if any remodeling occurs after implantation so that any resulting leaks are sealed.

It is a further object of the present invention to support fixation, anchoring or landing platform of/for the TAV device, especially in individuals lacking sufficient calcification in the native valve and in individual with aortic insufficiency as a diseased state.

SUMMARY OF THE INVENTION

Expandable sealing means for endoluminal devices have been developed for controlled activation. These include a means for controlled activation at the site where the device is to be secured, and thereby avoids premature activation that could result in misplacement or leakage at the site. The sealing means for placement at least partially between an endoluminal prosthesis and a wall of a body lumen has a first relatively reduced radial configuration and a second relatively increased radial configuration which is activated by means of a wire or other similar means, by the pressure of expansion at the site of implantation, or simply by virtue of the expansion of the device, releasing a swellable material such as a hydrogel into the sealing means, for example, by rupture of a capsule containing the swellable material, which then swells upon contact with fluid at the site to expand the sealing means into secure contact with the lumen walls. Gels having the desired mechanical and swellable properties have been developed, as demonstrated by the examples. The sealing means is particularly advantageous since it expands into sites to eliminate all prosthetic-annular incongruities, as needed. A major advantage of these devices is that the sealing means creates little to no increase in profile, since it remains flat/inside or on the device until the sealing means is activated.

Exemplary endoluminal devices including the sealing means for controlled activation that have been developed include stents, stent grafts for aneurysm treatment and transcutaneously implanted aortic valves (TAV) or mitral, tricuspid or pulmonary valves. In all embodiments, the sealing means is configured to maintain the same low profile as the device without the sealing means. In a preferred embodiment, the sealing means is positioned posterior to the prosthetic implant, and is expanded or pulled up into a position adjacent to the implant at the time of placement/deployment or sealing. This is achieved using sutures or elastic means to pull the seal up and around the implant at the time of placement, having a seal that expands up around implant, and/or crimping the seal so that it moves up around implant when the implant comes out of introducer sheath. This is extremely important with large diameter implants such as aortic valves, which are already at risk of damage to the blood vessel walls during transport. In another embodiment, the seal is placed around the skeleton of the TAV, so that it expands with the skeleton at the time of implantation of the TAV. In a variation of this embodiment, the seal is placed between the TAV and the skeleton, and expands through the skeleton sections at the time of implantation to insure sealing. In all embodiments, it is absolutely critical that the hydrogel/exapandable material operates under sufficient low pressure so that it does not push the stent away from the wall or alter the device configuration.

In yet another embodiment, a mechanism enables both deployment and retrieval of the system. This is particularly important from the ease of use and placement accuracy perspective. This feature enables the physician to change/alter the placement of the device in vivo if it was not properly positioned in the first attempt. Also, in the event of some complication during the operation, the physician can completely retrieve the device out of the patient (even after the "expandable material" has completely expanded).

These devices have the advantages of providing excellent sealing in combination with a low profile, controlled or contained release, and active conforming to leak sites to eliminate prosthetic-annular incongruence. If vascular re-modeling occurs over time, which could lead to leakage, the seal will also remodel, preventing leaks from developing. For devices that are at high risk of leakage, a pleated or accordion-like design provides for even better coverage and prevents uneven distribution of seal filler.

BRIEF DESCRIPTION OF THE DRAWINGS

FIGS. 1A, 1B and 1C are perspective views of a transcatheter aortic valve (TAV) (FIG. 1A), a controlled activatable seal (FIG. 1B), and the seal placed around the TAV (FIG. 1C).

FIGS. 5A-5E are perspective views of a method depicting a "method" to crimp and load the device with the "activation wire". The "activation wire" has to be shortened in length during the crimping/loading process so that the "activation or rupture" can be triggered during deployment/placement of the device. Before crimping/loading the "activation wire" is long enough so that the "activation mechanism" is far from activation and the hydrogel can remain completely sealed/deactivated during stor

FIGS. 7A-7D are perspective views of an impermeable sealing system to protect the implantable device during storage in a preservative solution such as glutaraldehyde, seals in place (FIG. 7A); exterior seal being removed (FIG. 7b); exterior seal removed and interior seals being removed (FIGS. 7C, 7D).

FIG. 8 is a cross-sectional view of the exterior and interior seals of FIGS. 7A-7D.

FIGS. 9A-9D are schematics of the placement of a Sapien valve with and without the disclosed sealing means. When the Sapien valve is placed too low into the LVOT leading to the graft skirt not completely apposing against the vasculature (FIG. 9A), perivalvular leak may occur from the gaps/area above the skirt and around the device, through the open cells of the stent (FIG. 9b). The Sapien valve with sealing means, even when placed too low into the LVOT, seals the valve uniformly against the inner wall of the LVOT (FIG. 9C). FIG. 9D shows how no perivalvular leak occurs when the seal is in place, preventing the "leaking" blood from going back into the left ventricle.

FIG. 10A shows a correctly placed SJM/Medtronic TAV device. FIG. 10b depicts an incorrectly placed SJM/Medtronic TAV device, resulting in PV leaks. FIG. 10C shows how perivascular leaks are prevented with an incorrectly placed SJM/Medtronic TAV device with sealing means.

FIGS. 11A and 11B are prospective views of a self-aligning support member design for self-expanding TAV prosthesis, which enables system deployment and retrieval without the use of "activation sutures".

FIGS. 12A-12F are prospective view of the self-aligning support as it is deployed, showing how the self-aligning support members are deployed from the catheter first to align the catheter and subsequently the frame of the prosthetic exits and extends outwardly and over the support members to position the prosthetic.

DETAILED DESCRIPTION OF THE INVENTION

I. Endoluminal Device Seal

A. Endoluminal Devices

Endoluminal prosthesis and sealing devices are advanced through a body lumen in a first undeployed and reduced profile configuration. When positioned in situ, the sealing device expands from its reduced radial profile configuration to a second configuration with an increased radial profile. In situ, and in its second configuration, the sealing device is configured to be positioned between the prosthesis and the wall of the body lumen. In one embodiment, when the endoluminal prosthesis is at the desired location in the body lumen, it is typically deployed from an introducer catheter whereupon it may move to an expanded radial configuration by a number of mechanisms. In some embodiments, the prosthesis may be spring expandable. Alternatively, a balloon or expandable member can be inflated within the lumen of the prosthesis to cause it to move to an expanded radial configuration within the vessel. This radial expansion, in turn, presses the sealing device against a wall of the body lumen. One of the advantages of the seal is that it only fills the gaps, and does not impact the placement and integrity—both physical and functional, of the prosthetic or the implant.

In one embodiment, the sealing device is configured to fully seal a proximal, central and/or distal end of the endoluminal prosthesis for endovascular aneurysm repair (EVAR) to prevent endoleaks and prevent subsequent migration and/or dislodgement of the prosthesis.

In another embodiment, the sealing device is configured to fully seal a transcatheter aortic valve. FIGS. 1A, 1B and 1C are perspective views of a transcatheter aortic valve (TAV) 10 (FIG. 1A), a controlled activatable seal (FIG. 1B) 12, and the seal placed around the TAV 14 (FIG. 1C).

Figure 2A:
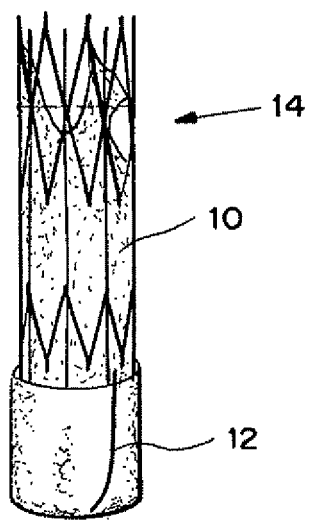
FIGS. 2A, 2B and 2C are perspective views of the TAV of FIG. 1C crimped toward the inflow side of the TAV in a telescopic manner (FIG. 2A), with the TAV and seal in an expanded state with the stent aligned with the bottom section of the TAV, with the activation wire activated to expose the seal to fluids (FIG. 2B), and post deployment, with the seal expanded by swelling of the hydrogel within the seal when it contacts the blood.
Figure 2B:
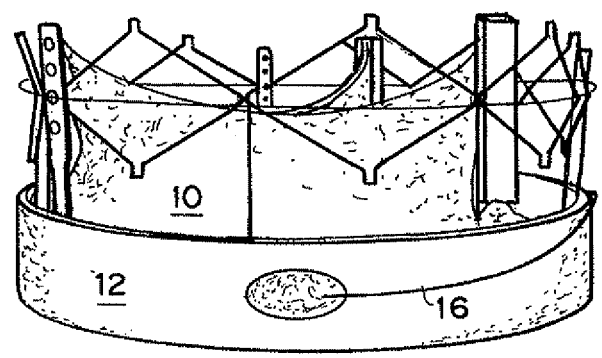
Figure 2C:
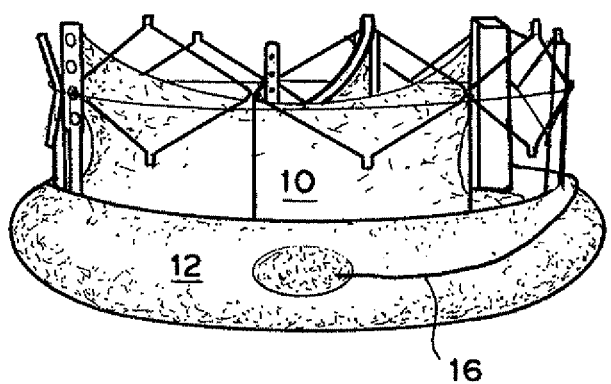

FIGS. 2A, 2B and 2C are perspective views of the TAV 14 of FIG. 1C crimped toward the inflow side of the TAV 10 in a telescopic manner (FIG. 2A), with the TAV 10 and seal 12 in an expanded state with the stent aligned with the bottom section of the TAV, with the activation wire 16 activated to expose the seal 12 to fluids (FIG. 2B), and post deployment, with the seal 12 expanded by swelling of the hydrogel within the seal when it contacts the blood.

The endoluminal device may be configured such that it moves independently of the endoluminal prosthesis. Alternatively, the endoluminal device may be connected to the prosthesis for delivery to a target site. The endoluminal device may be connected to the prosthesis by any number of means including suturing, crimping, elastic members, magnetic or adhesive connection.

In one embodiment, the sealing means is positioned posterior to the prosthetic implant, and is expanded and pulled up into a position adjacent to the implant at the time of sealing. This is achieved using sutures or elastic means to pull the seal up and around the implant at the time of placement, having a seal that expands up around implant, and/or crimping the seal so that it moves up around implant when implant comes out of introducer sheath. This is extremely important with large diameter implants such as aortic valves, which are already at risk of damage to the blood vessel walls during transport.

A key feature of the latter embodiment of the seal technology is that it enables preservation of the crimped profile of the endoluminal prosthesis. The seal technology is crimped distal or proximal to the prosthesis. In one aspect of this technology, the seal is aligned with the prosthesis by expansion of the seal. In another aspect, the seal zone of the prosthesis is aligned with the seal zone prior to expansion of the prosthesis by use of activation members. In yet another embodiment, the seal is aligned with the seal zone of the prosthesis prior to prosthesis expansion by use of activation members, which can be made of an elastic or non-elastic material.

In additional embodiments, the seal is positioned between the device skeleton and the device, or on the exterior of the skeleton.

In a further embodiment, the endoluminal device may further include one or more engagement members. The one or more engagement members may include staples, hooks or other means to engage with a vessel wall, thus securing the device thereto.

B. The Seal

The seal includes a flexible component that is configured to conform to irregularities between the endoluminal prosthesis and a vessel wall. The seal includes a generally ring-like structure having a first or inner surface and a second or outer surface. It contains a material that swells upon contact with a fluid or upon activation of a foam, following placement, to inflate and conform the seal around the device.

Figure 3:
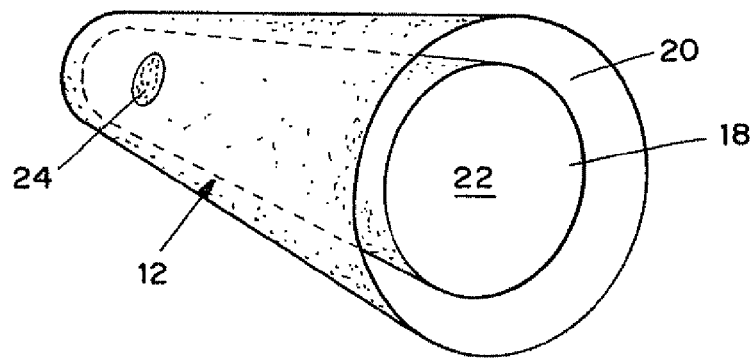
FIG. 3 is a perspective cross-sectional view of the seal, showing the inner and outer membranes, hydrogel within the inner membrane and the rupture/activation site.

As shown in FIG. 3, the seal 12 is a capsule-within-a capsule. The seal 12 can be provided in a variety of shapes, depending on the device it is to be used with. A "D" shape is the preferred embodiment, with the flat portion being attached to the support structure and/or device to be implanted.

The seal can be composed of a permeable, semi-permeable, or impermeable material. It may be biostable or biodegradable. For example, the seal may be composed of natural or synthetic polymers such as polyether or polyester polyurethanes, polyvinyl alcohol (PVA), silicone, cellulose of low to high density, having small, large, or twin pore sizes, and having the following features: closed or open cell, flexible or semi-rigid, plain, melamine, or post-treated impregnated foams. Additional materials for the seal can include polyvinyl acetal sponge, silicone sponge rubber, closed cell silicone sponges, silicone foam, and fluorosilicone sponge. Specially designed structures using vascular graft materials including polytetrafluoroethylene (PIPE), polyethylterephthalate (PET), polyether ether ketone (PEEK), woven yarns of nylon, polypropylene (PP), collagen or protein based matrix may also be used. PEEK is the preferred material at this time since the strength is high so that there will be no damage leading to failure when the TAV device is expanded against sharp/calcified nodules and at the same time a relatively thin sheet of material can be used, helping maintain a lower profile.

The seal material may be used independently or in combination with a mesh made from other types of polymers, titanium, surgical steel or shape memory alloys.

In other embodiments, the capsule may be segmented to include one or more compartments. The compartments may be relatively closely spaced. Further, the distance between adjacent compartments may vary. The segmented capsule of this embodiment may not extend completely around the endoluminal prosthesis when the support member is in its second increased radial configuration. In one embodiment wherein the support member includes a capsule, the capsule may be substantially surrounded by the support member. In other embodiments, however, the capsule may be only partially enveloped by the support member.

The capsule may include an outer wall to hold the agent therein. The outer wall may be made of a suitably flexible and biocompatible material. Alternatively, the capsule may include a more rigid structure having a pre-designed failure mechanism to allow the release of agent therefrom. Examples of suitable materials include, but are not limited to, low density polyethylene, high density polyethylene, polypropylene, polytetrafluoroethylene, silicone, or fluorosilicone. Other fluoropolymers that may be used for the construction of the capsule include: polytetrafluoroethylene, perfluoroalkoxy polymer resin, fluorinated ethylene-propylene, polyethylene-tetrafluoroethylene, polyvinylfluoride, ethylenechlorotrifluoroethylene, polyvinylidene fluoride, polylychlorotrifluoroethylene, perfluoropolyether, fluorinated ethylene propylene, terpolymer of tetrafluoroethylene, hexafluoropropylene and vinylidene fluoride), polysulphone and polyether ether ketone (PEEK). It may also include non-polymeric materials such as glass, bioglass, ceramic, platinum and titanium. It may further include biologically based materials such as crosslinked collagen or alginates. It will be appreciated that the foregoing list is provided merely as an example of suitable materials and is not an exhaustive list. The capsule may be composed of a material or combination of materials different from those provided above.

The rate of release of the agent from the support member may vary. In some embodiments, pressure exerted on the support member to rupture a capsule may release one or more agents. This rate of almost immediate release is particularly useful for delivering adhesive agents to a vessel to affix a prosthesis to a wall of the vessel. However, other agents may be released at a slower or at least a variable rate. Further, the agents may be released after the initial release of a primary agent (e.g. the adhesive).

For example, in an embodiment wherein the support member includes a segmented capsule, the first agent to be released may be held in one or more "immediate release" sub-compartments which include an outer wall configured to rupture under a pre-defined initial pressure. The support member may include one or more slow release sub-compartments having outer walls configured to withstand the initial pressure but which either rupture when subjected to a greater pressure or which do not rupture but rather degrade over a certain period of time to release an agent held therein.

Typically, the capsule is configured to rupture to release one or more agents at a predetermined range of pressures. The range of rupture pressures includes between 5 and 250 psi, between 5 and 125 psi, between 10 and 75 psi, or at approximately 50 psi.

A variety of different techniques or processes can be used to form pressure activated capsules or compartments. In one embodiment, for example, a process for forming a pressure activated capsule includes pre-stressing the capsule during formation. The pre-stressed material will have a limited capacity to stretch when subjected to external pressure, and will fail when reaching critical stress on the stress-strain curve. The first stage of this method includes selecting a biocompatible capsule material that is also compatible with its contents (e.g., the agent which can include adhesive material or a wide variety of other types of materials). The capsule material should also have a tensile strength suitable for the particular application in which the capsule will be used.

The next stage of this method includes forming an undersized capsule. The undersized capsule is essentially shaped as an extruded, elongated tube (e.g., a "sausage") with one end of the tube sealed (e.g., by dipping, dip molding, vacuum forming blow molding, etc.). The process continues by expanding the capsule to its final shape. The capsule can be expanded, for example, by stretching (e.g., either hot or cold) using appropriate tooling so that the capsule material is pre-stressed to within a stress level, and whereby the clinically relevant balloon inflation pressure will exceed the failure stress of the capsule material. The method can further include filling the capsule with the desired contents while the capsule is under pressure so as to achieve pre-stressing in a single step. After filling the capsule, the capsule can be sealed (e.g., using a heat welding process, laser welding process, solvent welding process, etc.).

In another embodiment, a capsule can be formed by forming an air pillow or bubble wrap-type capsule assembly using a vacuum form process or other suitable technique. The next stage of this process includes perforating a film at the base of the capsule assembly and filling the individual capsules with the desired contents under an inert atmosphere. After filling the capsules, the puncture hole can be resealed by application of another film over the puncture hole and localized application of heat and/or solvent. Other methods can be used to seal the puncture hole. In several embodiments, the capsule can be configured such that the puncture hole re-ruptures at the same pressure as the capsule itself so that there is some agent (e.g., adhesive material within the capsule) flowing onto the corresponding portion of the endoluminal prosthesis.

One or more failure points can be created within a capsule. This process can include creating a capsule shaped as an extruded, elongated tube with one end of the tube sealed (e.g., by dipping, dip molding, vacuum forming blow molding, etc.). The capsule can be composed of a polymer material (e.g., polyethylene, polypropylene, polyolefin, polytetrafluoroethylenes, and silicone rubber) or another suitable material. At one or more predetermined locations along the elongated tube, the process can include creating areas of substantially reduced thickness. These areas can be formed, for example, using a tool (e.g., a core pin with a razor blade finish along the length of the capsule), laser ablation, creating partially penetrating holes, creating an axial adhesive joint (e.g., tube from a sheet) that is weaker than the substrate, or other suitable techniques. The method next includes filing the capsule with the desired contents at a pressure below that required to rupture the thinned or weakened areas. After filling the capsule, the open end of the capsule can be sealed using one of the welding processes described above or other suitable processes.

In yet another particular embodiment, one or more stress points can be created within a capsule. This method can include forming a capsule and filling the capsule with the desired contents using any of the techniques described above. After forming the capsule and with the capsule in an undeployed configuration, the process can further include wrapping a suture (e.g., a nitinol wire) about the capsule at a predetermined pitch and tension. When the capsule is moved from the undeployed state to a deployed configuration and takes on a curved or circumferential shape, the suture compresses the capsule at the predetermined points. Stress points are created in the capsule walls at these points because of the increased pressure at such points.

In another embodiment the device may include one or more pressure points on the supporting member such as spikes or other raised areas which cause the penetration of the capsule once a predetermined pressure is applied thereto.

Still yet another particular embodiment for forming a pressure activated capsule or compartment includes creating a double walled capsule in which an inner compartment of the capsule is sealed and separated from an outer compartment of the capsule that contains the adhesive or other desired agent. The inner compartment can be composed of a compliant or flexible material, and the outer compartment can be composed of a substantially less compliant material. The outer compartment may or may not have failure points. The inner compartment is in fluid communication via a one way valve with a low compliance reservoir. The reservoir is configured to be pressurized by inflation of an expandable member or balloon to a high pressure, thereby allowing the valve to open and pressurize and expand the inner compartment. This process in turn pressurizes the outer compartment (that contains the adhesive) until the outer compartment ruptures. One advantage of this particular embodiment is that it can increase the pressure within the capsule to a value higher than otherwise possible with an external expandable member or balloon alone.

In a still further embodiment, the capsule has an inner compartment made from a relatively rigid material or mesh and an outer compartment made from a relatively flexible material. In this embodiment, the inner compartment acts as a reservoir, containing the agent and is designed to break or rupture at a predetermined pressure. The outer compartment may also have a failure pressure point to allow release of the agent. The rigidity of the inner compartment may provide a longer-term stability and shelf life of the encapsulated agent. The application of rupture pressure may be carried out either locally or remotely, e.g. via a tube directly connected to the capsule that is connected to an external source at the delivery device entry site (e.g. femoral artery).

Expandable Capsule

The seal entirely surrounds the capsule such that the capsule is "suspended" within the seal. In one specific embodiment, for example, the seal 12 can include a porous material configured to prevent any embolization (distal or proximal) of released agent(s) 108 from the capsule 106. The seal may have a graded degree of relative porosity from relatively porous to relatively non-porous.

In the preferred embodiment, the capsule is a single annular compartment within the seal, and extends completely around the periphery of the endoluminal prosthesis. In other embodiments, however, the capsule may include one or more additional compartments or sections, and may not extend completely around the endoluminal prosthesis. Moreover, the capsule may or may not be contained within the seal, and can be positioned at a different location on the apparatus relative to the seal. In addition, the capsule can have a variety of different shapes and/or sizes depending upon the particular application, the agent(s), the configuration of the endoluminal prosthesis, and a number of other factors.

Permeable and Impermeable Membranes

In a preferred embodiment, shown in FIG. 3, the seal 12 includes two membranes, an inner membrane 18 and an outer membrane 20. An expandable material such as a foam or hydrogel 22 is placed within the inner membrane 18. The inner membrane 18 is semi-permeable (allowing fluid ingress but not egress of entrapped hydrogel or foam) while the outer membrane 20 is impermeable except at an optional pre-determined rupture point 24. The outer membrane 20 is designed to be impermeable to fluid during storage and transport and during any pre-procedural preparations e.g. rinsing or washing of the device, to protect the polymer 22 from premature swelling. The outer membrane 20 is also designed to be strong and puncture resistant so that it does not tear or is punctured or pierced by the sharp edges of the native calcification even when subject to pressures up to 14 atm. This prevents the rupture of the inner membrane 18, mitigating any risk of embolization of the expandable material or hydrogel 22. The rupture point 24 allows fluid such as blood to penetrate into the expandable seal only when the seal is expanded in place, thereby preventing leaks.

Permeable membranes may be made from a variety of polymer or organic materials, including polyimides, phospholipid bilayer, thin film composite membranes (TFC or TFM), cellulose ester membranes (CEM), charge mosaic membranes (CMM), bipolar membranes (BPM), and anion exchange membranes (AEM).

A preferred pore size range for allowing fluid in but not hydrogel to escape is between 50 and 70 microns.

The permeable membrane may be formed only of permeable material, or may have one or more areas that are impermeable. This may be used to insure that swelling does not disrupt the shape of the seal in an undesirable area, such as on the interior of the device where it abuts the implant or prosthesis, or where it contacts the device support members.

In some embodiments, the second impermeable membrane is applied with plasma vapour deposition, vacuum deposition, co-extrusion, or press lamination.

Expandable Materials

Hydrogels which swell in contact with an aqueous fluid are the preferred materials since blood or other fluids at the site of implantation can penetrate into the seal after it is breached so that the hydrogel absorbs the saline in the blood or other body fluids and swells. The semi-permeable inner membrane 18 prevents hydrogel 22 from escaping the seal 12 but allows fluid to enter.

The properties of the hydrogel are selected to provide a rapid swell time as well as to be biocompatible in the event of breach of capsule integrity. Two or more hydrogels or other materials that swell may be used. Alternatively, one may use a foam. Foams may be designed to expand without the need for the semi-permeable membrane. The properties of the different materials will then complement each other. For example, in the time immediately after valve deployment it is important that the material swells quickly to seal perivalvular leaks as soon as possible. Mechanical strength may be compromised in the short term to enable fast swelling. In the long term, however, it is paramount that the seal has high mechanical strength. The mechanical strength should be high enough to allow swelling and thereby "actively" conform to the gaps leading to leakage but not high enough to disturb the physical or functional integrity of the prosthesis or implant or to push the prosthesis or implant away from the wall.

A degradable material, which may be a hydrogel, that swells quickly, may be used in conjunction with a nondegradable material, which may be a hydrogel, that swells slower but has higher mechanical strength. In the short term, the degradable material capable of rapid swelling will quickly seal the perivalvular leak. Over time, this material degrades and will be replaced by the material exhibiting slower swelling and higher mechanical strength. Eventually, the seal will be composed of the slower swelling nondegradable material. It is also possible to use only one material in the seal, but in two or more different forms. For example, two different crystal sizes of hydrogels may be used in the seal, because different particle sizes of hydrogel may exhibit different properties.

Studies to identify hydrogels having substantial swelling in a short time were performed, as described in examples 1 and 2. The main factors that influence swelling of a hydrogel based on polymerisation and cross-linking of synthetic monomers are:

(1) type of monomer;
(2) type of cross-linker;

(3) concentration of monomer and cross-linker in the gel; and (4) the ratio of monomer to cross-linker.

Examples of rapidly swelling hydrogels include, but are not limited to, acrylic acid polymers and copolymers, particularly crosslinked acrylic acid polymer and copolymers. Suitable crosslinking agents include acrylamide crosslinkers, di(ethylene glycol) diacrylate, poly(ethylene glycol) diacrylate, and long-chain hydrophilic polymers with multiple polymerizable groups, such as poly vinyl alcohol (PVA) derivatized with allyl glycidyl ether.

Other examples include changing the morphology of known hydrogel materials in order to decrease swelling times. Means for changing the morphology include increasing the porosity of the material, for example, by freeze-drying or porogen techniques.

Fast swelling can be achieved by preparing small particles of dried hydrogels. The extremely short diffusion path length of microparticles makes it possible to complete swelling in a matter of minutes.

Large dried hydrogels can be made to swell rapidly regardless of their size and shape by creating pores that are interconnected to each other throughout the hydrogel matrix. The interconnected pores allow for fast absorption of water by capillary force. A simple method of making porous hydrogel is to produce gas bubbles during polymerization. Completion of polymerization while the foam is still stable results in formation of superporous hydrogels. Superporous hydrogels can be synthesized in any moulds, and thus, three-dimensional structure of any shape can be easily made. The size of pores produced by the gas blowing (or foaming) method is in the order of 100 mm and larger.

If any portion of a superporous hydrogel is in contact with water or an aqueous medium, water is absorbed right away through the open channels to fill the whole space. This process makes the dried superporous hydrogels swell very quickly.

Alternatively, a foam generated in situ can also be used as a swellable material to form a seal. For example, a suitable matrix, such as a biocompatible polymer or crosslinkable prepolymer, may be blended with one or more foaming agents. Foaming agents include compounds or mixtures of compounds which generate a gas in response to a stimulus. When dispersed within a matrix and exposed to a stimulus, the foaming agents evolve a gas, causing the matrix to expand as fine gas bubbles become dispersed within the matrix. Examples of suitable foaming agents include compounds which evolve a gas when hydrated with biological fluids, such as mixture of a physiologically acceptable acid (e.g., citric acid or acetic acid) and a physiologically acceptable base (e.g., sodium bicarbonate or calcium carbonate). Other suitable foaming agents are known in the art, and include dry particles containing pressurized gas, such as sugar particles containing carbon dioxide (see, U.S. Pat. No. 3,012,893) or other physiologically acceptable gases (e.g., nitrogen or argon), and pharmacologically acceptable peroxides. In all embodiments, it is absolutely critical that the hydrogel/expandable material operates under sufficient low pressure so that it does not push the stent away from the wall or alter the device configuration. In summary, the expandable material is contained within a material, such as an semi-permeable or impermeable material so that it is retained at the site where it is needed to seal a leak. The material is selected based on the means for activation. If the material is expanded by mechanical shear or exposure to a foaming agent, these materials are provided internally within the seal, allowing an external activating agent such as an activation wire to disrupt the means for isolating the activation agent from the expandable material. If the material is activated by contact with fluid, no additional means for isolation are required if the device is stored dry prior to use, since it will activate in situ when exposed to body fluids. If the material is stored wet prior to use, a second impermeable membrane is required to keep the expandable material dry prior to activation. This will typically include a rupture site which is opened at the time of implantation to allow biological fluid to reach the expandable material through the semi-permeable material (i.e., where semi-permeable refers to a material retaining the expandable material but allowing fluid to pass). Alternatively the impermeable material may not include a rupture site but simply be removed after the device is removed from storage and washed with saline, prior to loading into the catheter, so that once the device is deployed, in situ liquid will cause the hydrogel to swell.

C. The Support Member or Skeleton

The seal may be sufficiently flexible to conform to irregularities between the endoluminal prosthesis and a vessel wall. The band of material may include a mesh-like or a generally ring-like structure configured to receive at least a portion of an endoluminal prosthesis such that it is positioned between the portion of the prosthesis and a vessel wall. This is usually referred to as a skeleton or support member.

Figures 4A, 4B, 4C:
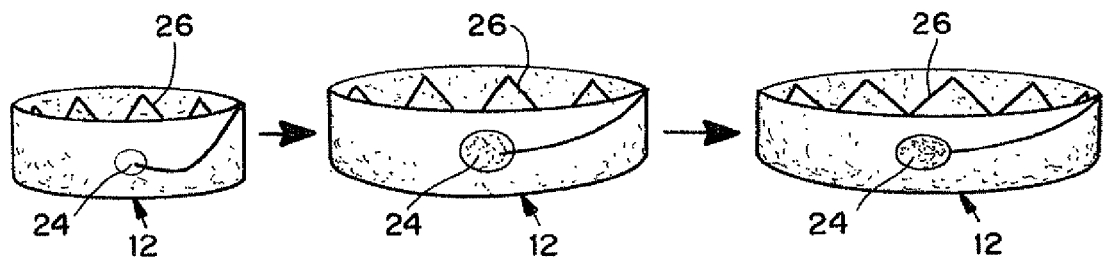
FIGS. 4A, 4B and 4C are perspective views of the seal prior to rupture and expansion of the seal (FIG. 4A), during application of pressure from a wire to rupture the swelling material container and with partial expansion of the seal (FIG. 4B), and after rupture of the swelling material container and with full expansion (FIG. 4C).

As shown in FIGS. 4A-4C, the seal 12 has a stent/metal backing or skeleton 26. The skeleton 26 provides structure and enables crimping, loading and deployment. The skeleton 26 can be either a balloon expanding or a self-expanding stent. The skeleton 26 is attached to the surface of the outer membrane 20.

When the support member is in the second reduced radial configuration, it may form a substantially helical configuration. The helical structure of the support member provides an internal passage therein to receive at least a portion of an endoluminal prosthesis. The support member may include steel such as MP35N, SS316LVM, or L605, a shape memory material or a plastically expandable material. The shape memory material may include one or more shape memory alloys. In this embodiment, movement of the shape memory material in a pre-determined manner causes the support member to move from the first reduced radial configuration to the second increased radial configuration. The shape memory material may include Nickel-Titanium alloy (Nitinol). Alternatively, the shape memory material may include alloys of any one of the following combinations of metals: copper-zinc-aluminium, copper-aluminium-nickel, copper-aluminium-nickel, iron-manganese-silicon-chromium-manganese and copper-zirconium. Additionally, titanium-palladium-nickel, nickel-titanium-copper, gold-cadmium, iron-zinc-copper-aluminium, titanium-niobium-aluminium, uranium-niobium, hafnium-titanium-nickel, iron-manganese-silicon, nickel-iron-zinc-aluminium, copper-aluminium-iron, titanium-niobium, zirconium-copper-zinc, nickel-zirconium-titanium.

At least part of the support member may also include any one of the following combinations of metals: Ag—Cd 44/49 at. % Cd; Au—Cd 46.5/50 at. % Cd; Cu—Al—Ni 14/14.5 wt. % Al and 3/4.5 wt. % Ni, Cu—Sn approx. 15 at % Sn, Cu—Zn 38.5/41.5 wt. % Zn, Cu—Zn—X (X=Si, Al, Sn), Fe—Pt approximately 25 at % Pt, Mn—Cu 5/35 at. % Cu, Pt alloys, Co—Ni—Al, Co—Ni—Ga, Ni—Fe—Ga, Ti—Pd in various concentrations, Ni—Ti (approximately 55% Ni). The shape memory material of the support member may act as a spine along the length of the support member.

The plastically-expandable or balloon-expandable materials may include stainless steel (316L, 316LVM, etc.), Elgiloy, titanium alloys, platinum-iridium alloys, cobalt chromium alloys (MP35N, L605, etc.), tantalum alloys, niobium alloys and other stent materials.

The support member may be composed of a biocompatible polymer such as polyether or polyester, polyurethanes or polyvinyl alcohol. The material may further include a natural polymer such as cellulose ranging from low to high density, having small, large, or twin pore sizes, and having the following features: closed or open cell, flexible or semi-rigid, plain, melamine, or post-treated impregnated foams. Additional materials for the support member include polyvinyl acetal sponge, silicone sponge rubber, closed cell silicone sponges, silicone foam, and fluorosilicone sponge. Specially designed structures using vascular graft materials such as PTFE, PET and woven yarns of nylon, may also be used.

At least part of the support member may be composed of a permeable material. Alternatively, at least part of the support member may be semi-permeable. In a further embodiment, at least part of the support member may be composed of an impermeable material.

The support member may further include semi-permeable membranes made from a number of materials. Example include polyimide, phospholipid bilayer, thin film composite membranes (TFC or TFM), cellulose ester membrane (CEM), charge mosaic membrane (CMM), bipolar membrane (BPM) or anion exchange membrane (AEM).

The support member may include at least a porous region to provide a matrix for tissue in-growth. The region may further be impregnated with an agent to promote tissue in-growth. The support member itself may be impregnated with the agent or drug. The support member may further include individual depots of agent connected to or impregnated in an outer surface thereof. In one embodiment wherein the support member includes one or more capsules, the agent may be released by rupturing of the capsule. Whether the agent is held in capsules, depots, in a coating or impregnated in the material of the support member, a number of different agents may be released from the support member. For example, in an embodiment wherein the support member includes a capsule, the capsule may include an annular compartment divided by a frangible wall to separate the compartment into two or more sub-compartments. A different agent may be held in each sub-compartment. In one embodiment, the annular compartment may be divided longitudinally with at least one inner sub-compartment and at least one outer sub-compartment. Alternatively, the capsule may be divided radially into two or more sub-compartments. The sub-compartments may be concentric relative to one another. In the embodiment wherein the capsule is segmented, the different compartments may hold different agents therein.

The support member may have hooks, barbs or similar/other fixation means to allow for improved/enhanced anchoring of the sealing device to the vasculature. In addition, the support member may serve as the "landing zone" for the device when there may be the need to position the device in a more reinforced base structure, for example, in the case of valves where there is insufficient calcification for adquate anchoring, short and angulated necks of abdominal and thoracic aortic aneurysms, etc.

In all embodiments, the support member may be connected to a graft or stent by a tethering member. The tethering member may be made of an elastomeric material. Alternatively, the tethering member may be non-elastomeric and have a relatively fixed length or an appropriately calculated one for desired activation mechanism.

In embodiments where a device support member includes a capsule, the capsule may include a single annular compartment within the support member. In this embodiment, when the support member is in its second increased radial configuration, the capsule extends completely around the periphery of the endoluminal prosthesis. Alternatively, the capsule may only partially extend around the periphery of the prosthesis. Two or more capsules may extend around the prosthesis.

Figure 6A:
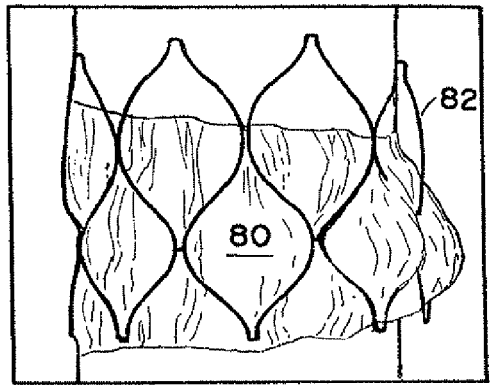
FIGS. 6A-6B are perspective views of a seal that is placed inside of the TAV device.
Figure 6B:
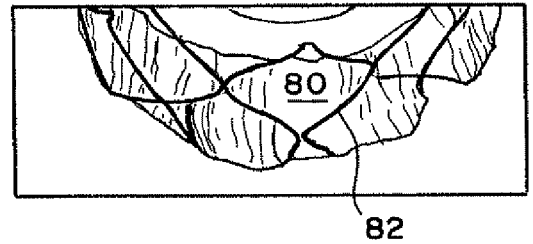
Figure 6C:
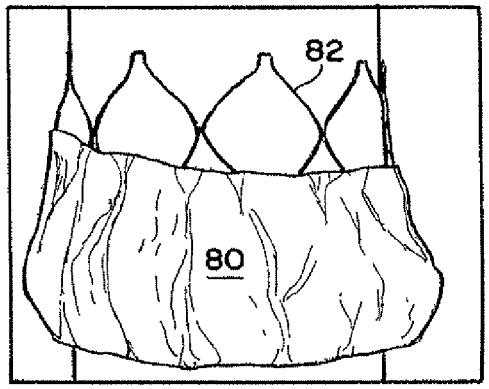
FIGS. 6C-6D are perspective views of a seal that is placed on the exterior of the TAV device.
Figure 6D:
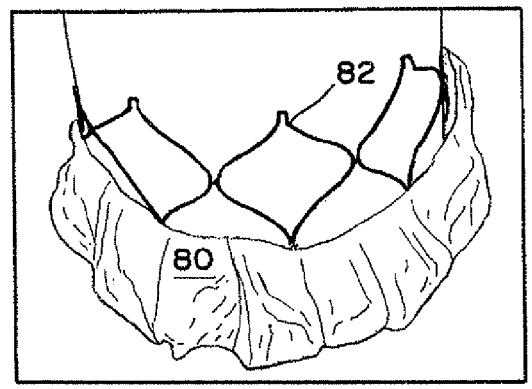

In other embodiments, shown in FIGS. 6A-6D, the capsule 80 may have an accordion-like structure to allow for wider, deeper expansion into the potential leak sites and also keep more room for expansion with any vascular re-modeling and thereby ensure constant and durable sealing. This can be positioned within the support structure 82 as shown in FIGS. 6A-6B or on the exterior of the support structure 82 as shown in FIGS. 6C-6D.

D. Agents to be Delivered by or with the Seal

The seal can further serve as a porous matrix for tissue in-growth and can aid in promoting tissue in-growth, for example, by adding growth factors, etc. This should improve the long-term fixation of the endoluminal prosthesis. For example, the seal can be impregnated with activators (e.g., adhesive activator) that induce rapid activation of the agent (e.g., a tissue adhesive) after the agent has been released from the capsule. In other embodiments, however, the seal can be composed of different materials and/or include different features.

The agent(s) in the capsule can include adhesive materials, tissue growth promoting materials, sealing materials, drugs, biologic agents, gene-delivery agents, and/or gene-targeting molecules. In another embodiment, the one or more agent may be sheathed for delivery to a target site. Once positioned at the target site, the one or more agent may be unsheathed to enable release to the surrounding environment. This embodiment may have particular application for solid or semi-solid state agents.

1. Adhesives

Adhesives that may be used to aid in securing the seal to the lumen, or to the device to be implanted include one or more of the following cyanoacrylates (including 2-octyl cyanoacrylate, n-butyl cyanoacrylate, iso-butyl-cyanoacrylate and methyl-2- and ethyl-2-cyanoacrylate), albumin based sealants, fibrin glues, resorcinol-formaldehyde glues (e.g., gelatin-resorcinol-formaldehyde), ultraviolet-(IJV) light-curable glues (e.g., styrene-derivatized (styrenated) gelatin, polyethylene glycol)diacrylate (PEGDA), carboxylated camphorquinone in phosphate-buffered saline (PBS), hydrogel sealants-eosin based primer consisting of a copolymer of polyethylene glycol with acrylate end caps and a sealant consisting of polyethylene glycol and polylactic acid, collagen-based glues and polymethylmethacrylate.

2. Bioactives

The agent(s) released from the seal or support member may include one or more pharmaceutical, prophylactic, or diagnostic materials such as tissue growth promoting materials, drugs, and biologic agents, gene-delivery agents and/or gene-targeting molecules, more specifically, vascular endothelial growth factor, fibroblast growth factor, hepatocyte growth factor, connective tissue growth factor, placenta-derived growth factor, angiopoietin-1 or granulocyte-macrophage colony-stimulating factor.

Agents for modulating cellular behaviour include microfibrillar collagen, fibronectin, fibrin gels, synthetic Arg-Gly-Asp (RGD) adhesion peptides, tenascin-C, Del-1, CCN family (e.g., Cyr61) hypoxia-inducible factor-1, acetyl choline receptor agonists and monocyte chemoattractant proteins. Gene delivery agents include viral vectors for gene delivery (e.g., adenoviruses, retroviruses, lentiviruses, adeno-associated viruses) and non-viral gene delivery agents/methods (e.g., polycation polyethylene imine, functional polycations, consisting of cationic polymers with cyclodextrin rings or DNA within crosslinked hydrogel microparticles, etc.).

Agents modulating cell replication/proliferation include targets of rapamycin (TOR) inhibitors (including sirolimus, everolimus and ABT-578), paclitaxel and antineoplastic agents, including alkylating agents (e.g., cyclophosphamide, mechlorethamine, chlorambucil, melphalan, carmustine, lomustine, ifosfamide, procarbazine, dacarbazine, temozolomide, altretamine, cisplatin, carboplatin and oxaliplatin), antitumor antibiotics (e.g., bleomycin, actinomycin D, mithramycin, mitomycin C, etoposide, teniposide, amsacrine, topotecan, irinotecan, doxorubicin, daunorubicin, idarubicin, epirubicin, mitoxantrone and mitoxantrone), antimetabolites (e.g., deoxycoformycin, 6-mercaptopurine, 6-thioguanine, azathioprine, 2-chlorodeoxyadenosine, hydroxyurea, methotrexate, 5-fluorouracil, capecitabine, cytosine arabinoside, azacytidine, gemcitabine, fludarabine phosphate and aspariginase), antimitotic agents (e.g., vincristine, vinblastine, vinorelbine, docetaxel, estramustine) and molecularly targeted agents (e.g., imatinib, tretinoin, bexarotene, bevacizumab, gemtuzumab ogomicin and denileukin diftitox).

In one embodiment the one or more agents may include monoclonal antibodies. For example the monoclonal antibody may be an angiogenesis inhibitor such as Bevacizumab or have anti-inflammatory properties. Further examples of specific monoclonal antibodies include, but are not limited to, Adalimumab, Basiliximab, Certolizumab pegol, Cetuximab Daclizumab, Eculizumab, Efalizumab, Gemtuzumab, Ibritumomab tiuxetan, Infliximab Muromonab-CD3, Natalizumab, Omalizumab, Palivizumab, Panitumumab, Ranibizumab, Rituximab, Tositumomab or Trastuzumab.

The agent(s) may be steroids such as corticosteroids, estrogens, androgens, progestogens and adrenal androgens. The agent(s) may include antiplatelet, antithrombotic and fibrinolytic agents such as glycoprotein inhibitors, direct thrombin inhibitors, heparins, low molecular weight heparins, platelet adenosine diphosphate (ADP) receptor inhibitors, fibrinolytic agents (e.g., streptokinase, urokinase, recombinant tissue plasminogen activator, reteplase and tenecteplase, etc).

Additionally, gene targeting molecules such as small interference RNA, micro RNAs, DNAzymes and antisense oliogonucleotides, or cells such as progenitor cells (e.g., endothelial progenitor cells, CD34+ or CD133+monocytes, hemopoietic stem cells, mesenchymal stem cells, embryonic stem cells, multipotent adult progenitor cells and inducible pluripotent stem cells) and differentiated cells (e.g., endothelial cells, fibroblasts, monocytes and smooth muscle cells) may be agent(s). Furthermore, drug delivery agents like mucoadhesive polymers (e.g., thiolated polymers), or pharmacologic agents of local treatment of atherosclerosis such as high density lipoprotein cholesterol (HDL), HDL mimetics, heme oxygenase-1 inducers (e.g. probucol and its analogues, resveratol and its analogues), hydroxymethylglutaryl CoA (HMG-CoA) reductase inhibitors and fibrates (including fenofibrate, gemfibrozil, clofibrate etc) may be included agents.

The agent(s) may also modulate cellular behavior in relation to bioprosthesis, such as microfibrillar collagen, fibronectin, fibrin gels, synthetic Arg-Gly-Asp (RGD) adhesion peptides, tenascin-C, Del-1, CCN family (e.g., Cyr61) hypoxia-inducible factor-1, acetyl choline receptor agonists and monocyte chemoattractant proteins.

E. Additional Encapsulation of Sealing Means for Increased Shelf-Life

The seal may be sterile packaged for distribution and use. In the alternative, it may be packaged as part of, or in a kit with, the device it is designed to seal, such as a TAV or stent. This additional encapsulation prevents the activation of the expandable material during storage within solutions (e.g. glutaraldehyde, alcohol) by acting as a 100% moisture barrier.

Heart valves, both transcatheter and surgical, are stored in glutaraldehyde or similar solutions primarily to preserve the tissue component of the device. Before the device is implanted, it is prepared for implantation by removing it from the solution and rinsing it thoroughly so that all the glutaraldehyde is washed off.

Although the outer impermeable layer of the sealing device/capsule is meant to prevent any penetration of water from the glutaraldehyde into the capsule, there is a likelihood that the thickness may be insufficient given the profile constraints and as a result there may only be a limited shelf-life that may be obtained. In order to obtain an increased shelf-life where the encapsulated expandable material remains in its desirable unexpanded state until introduced within the body, an additional impermeable layer may be needed. This additional impermeable layer is not required once the device is removed out of the storage solution, and is rinsed to wash all the glutaraldehyde away. This will typically be removed after removing the device from the storage fluid and just before implantation.

To make the sealing means low profile, the thickness of the outer and inner membranes has to be kept to the minimum. If the sealing device is stored submerged in a solution, as in the case with transcatheter valves, for its shelf-life, the low profile, thin membranes may allow moisture to permeate through them and thereby risk the premature activation of the sealing means. Therefore, an additional means is necessary to ensure the appropriate shelf-life of the sealing device can be obtained.

As shown in FIGS. 7A-7D and 8, this additional means can be an additional layer 92 of encapsulation over the "impermeable" outer membrane 94. This additional layer 92 may be much thicker and may be laminated by metallic layers several microns in thickness to make it 100% moisture impermeable.

This additional encapsulation layer is removable and is designed to have a mechanism which enables easy peeling of the hermetic sealing capsule/layer so that this layer can be removed just before loading and crimping of the prosthesis into the delivery catheter, before it is delivered into the vasculature. The layer can be removed using different means, including peeling off, cracking off, melting off, vapouring off after the rinsing process is complete and the device is ready to load.

The additional encapsulation layer may be designed with a mechanism so that it can be attached to the device assembly with the sealing means during the assembly process by suturing or other appropriate means such that the removal process insures that integrity of the sealing means and its assembly with the base device remains completely intact.

A moisture impermeable film composite comprises a combination of polymer films, metalized polymer films and metal films. The polymer layers can be comprised of, but not limited to; Polyether ether ketone (PEEK), Polyethylene terephthalate (PET), Polypropylene (PP), Polyamide (PI), Polyetherimide (PEI) or Polytetrafluoroethylene (PTFE). Polymer films may or may not be mineral filled with either glass or carbon. Polymer films will have a thickness of 6 um or above. Metal films and coatings include aluminum, stainless steel, gold, mineral filled (glass & carbon) and titanium with a thickness of gum or above. Coatings can be applied with processes such as plasma vapor deposition, press lamination, vacuum deposition, and co-extrusion. Metal films can be laminated to polymer films via press lamination.

E. Devices for Placement of Devices with Sealing Means

Embodiments which Position Seal at Time of Implant

In a preferred embodiment, the sealing means is positioned posterior to the prosthetic implant, and is expanded or pulled up into a position adjacent to the implant at the time of sealing. This is achieved using sutures or elastic means to pull the seal up and around the implant at the time of placement, having a seal that expands up around implant, and/or crimping the seal so that it moves up around implant when implant comes out of introducer sheath. This is extremely important with large diameter implants such as aortic valves, which are already at risk of damage to the blood vessel walls during transport.

A key feature of the latter embodiment of the seal technology is that it enables preservation of the crimped profile of the endoluminal prosthesis. The seal technology is crimped distal or proximal to the prosthesis. In one aspect of this technology, the seal is aligned with the prosthesis by expansion of the seal. In another aspect, the seal zone of the prosthesis is aligned with the seal zone prior to expansion of the prosthesis by use of activation members. In yet another embodiment, the seal is aligned with the seal zone of the prosthesis prior to prosthesis expansion by use of activation members, which can be made of an elastic or non-elastic material.

In a further embodiment, the endoluminal device may further include one or more engagement members. The one or more engagement members may include staples, hooks or other means to engage with a vessel wall, thus securing the device thereto.

As shown in FIGS. 11A and 11B, self-aligning support members 82 made of Nitinol eliminate the use of attachment sutures within the catheter 80. The dual-membrane capsule containing the hydrogel can be attached to these members and is activated with the expansion of the prosthesis. The self-aligning members 82 can be directly laser-cut as part of the prosthesis frame 84 or can be connected using sutures. The primary advantage of this mechanism is that it eliminates any failure mode with the "activation member" (sutures, etc.) that enables the alignment of the capsule with the distal/proximal/middle section of the prosthesis.

Mechanisms for Deployment and Retrieval

In yet another embodiment, a mechanism enables both deployment and retrieval of the system. This is particularly important from the ease of use and placement accuracy perspective. This feature enables the physician to change/alter the placement of the device in vivo if it was not properly positioned in the first attempt. Also, in the event of some complication during the operation, the physician can completely retrieve the device out of the patient (even after the "expandable material" has completely expanded).

The key features when used with a self-expanding prosthesis:
1. system re-positionability (if the prosthesis is partially retrieved back in the catheter)—that enables accurate/precise placement of the device in the anatomy
2. system retrievability (both the prosthesis and the els SEAL capsule can be completely captured back into the catheter and retrieved out of the body).

II. Methods of Use

The device and seal can be utilized for sealing in a variety of tissue lumens, including cardiac chambers, cardiac appendages, cardiac walls, cardiac valves, arteries, veins, nasal passages, sinuses, trachea, bronchi, oral cavity, esophagus, small intestine, large intestine, anus, ureters, bladder, urethra, vagina, uterus, fallopian tubes, biliary tract or auditory canals. In operation, the endoluminal prosthesis is positioned intravascularly within a patient so that the prosthesis is at a desired location along a vessel wall. A balloon or other expandable member is then expanded radially from within the endoluminal prosthesis to press or force the apparatus against the vessel wall. As the balloon expands, the activation wire is triggered, rupturing the capsule and causing the seal to swell, and in some embodiment, releasing agents. In one embodiment, the agent includes an adhesive material and when the capsule ruptures, the adhesive material flows through the pores of the seal. As discussed above, the seal can control the flow of the adhesive to prevent embolization of the adhesive material.

In specific embodiments, the device may be used to seal a graft or stent within an aorta of a patient. In a further embodiment, the device may be used to seal an atrial appendage. In this embodiment, the device may deliver an agent to effect the seal of a prosthetic component across the opening to the atrial appendage.

In a further embodiment, the device may be used to seal a dissection in a vessel. In this embodiment, the support member is positioned adjacent the opening of the false lumen and an intraluminal stent subsequently delivered thereto. Upon radial expansion of the stent, the support member is caused to release adhesive therefrom to seal the tissue creating the false lumen against the true vessel wall.

In a further embodiment, the device is used to seal one or more emphysematous vessels.

In a still further embodiment, the device may be used to seal an artificial valve within a vessel or tissue structure such as the heart. An example includes the sealing of an artificial heart valve such as a TAV. It is envisaged that the seal provided by the present device will prevent paravalvular leaks.

As shown in FIGS. 4A-4C, the activation of the polymer 22 within the seal 12 takes place when a section of the outer membrane 20 is ruptured at the designated rupture point 24 using the activation wire 16. This is shown in FIG. 4A prior to rupture where the seal 12 is relatively flat; the designated rupture site 24 is opened as shown in FIG. 4B, then the seal 12 is expanded, as shown in FIG. 4C. The rupture site 24 is formed by weakening the surface of the membrane 20 at the site 24 using means such as a laser to partially cut into or perforate the membrane 20. An activation wire 16 is secured to the rupture site 24 by means of an adhesive, suture, or restraining means such as a brad, rivet, staple or clamp. The rupture site 24 is opened at a pre-determined pressure or location by pulling of the active wire, typically connected to the prosthesis or a part of the placement catheter.

FIGS. 5A-5E depict a method to crimp and load the device with the "activation wire" 16. The activation wire 16 has to be shortened in length during the crimping/loading process so that the "activation or rupture" can be triggered during deployment/placement of the device. Before crimping/loading the activation wire 16 is long enough so that the "activation mechanism" is far from activation and the hydrogel in the seal 14 can remain completely sealed/de-activated during storage and shelf-life.

The metal crimp is used to shorten the length of the activation wire 16 during the crimping/loading procedure. During storage the metal crimp in the "uncrimped" state and after the completion of the insertion of the device into the catheter it is "crimped" and the excess activation wire 16 is cut off. After this step the final steps of completely loading the TAV device in the catheter are completed and the device is ready to be inserted into the patient.

The device with seal is inserted in a manner typical for the particular device. After reaching the implantation site, the seal is ruptured and the seal expands to seal the site. The guidewire and insertion catheter are then withdrawn and the insertion site closed.

FIGS. 9A-9D are diagrams of the placement of a Sapien valve 50 with and without the disclosed sealing means 52. When the Sapien valve 50 is placed too low into the LVOT leading to the graft skirt not completely apposing against the vasculature (FIG. 9A), perivalvular leaking will occur from the gaps/area above the skirt and around the device, through the open cells of the stent (FIG. 9B). As shown in FIG. 9C, the Sapien valve 50 with sealing means 52, even when placed too low into the LVOT, seals the valve 50 uniformly against the inner wall of the LVOT. FIG. 9D shows how no perivalvular leak occurs when the seal 52 is in place, preventing the "leaking" blood from going back into the left ventricle.

Analogous results are obtained with the SJM/Medtronic TAV device. FIG. 10A shows a correctly placed SJM/Medtronic TAV device 60. FIG. 10B depicts an incorrectly placed SJM/Medtronic TAV device 60, resulting in PV leaks. FIG. 10C shows how perivascular leaks are prevently with an incorrectly placed SJM/Medtronic TAV device 60 with sealing means 62.

Figure 6E:
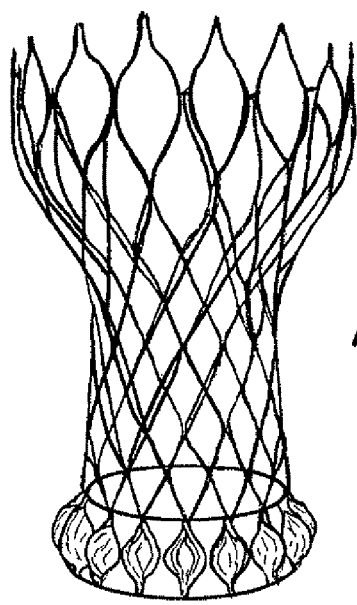
FIG. 6E shows the seal placed on the inside of the device such that the outer impermeable membrane is moulded to the stent scaffold and protrudes from within, in alignment with the stent pattern, while the inner permeable membrane remains in abutment with the inner circumference of the device. Hydrogels expand and cause the balloons to pop out.
Figure 13A:
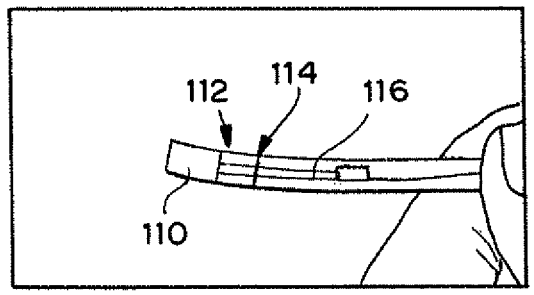
FIGS. 13A-13E are photographs of the deployment of the TAV using the sealing support members to position seal at time of placement.
Figure 13B:
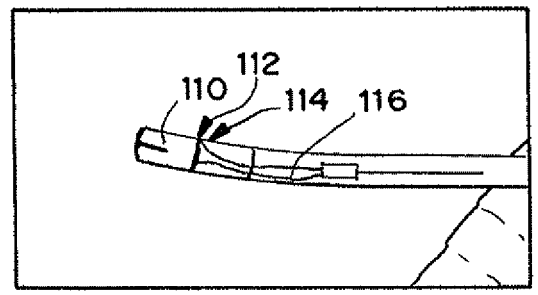
Figure 13C:
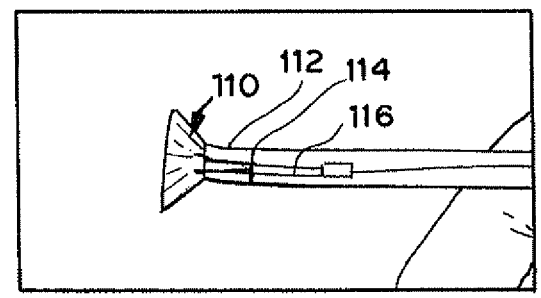
Figure 13D:
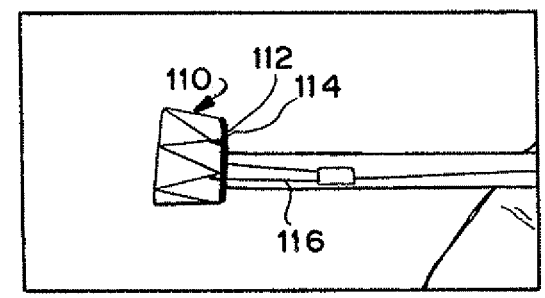
Figure 13E:
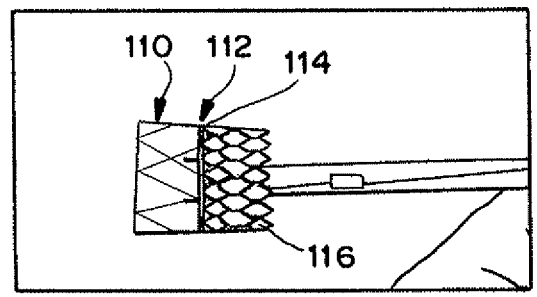

FIGS. 6A-6B are perspective views of a seal that is placed inside of the TAV device. FIGS. 6C-6D are perspective views of a seal that is placed on the exterior of the TAV device. FIG. 6E shows the seal placed on the inside of the device such that the outer impermeable membrane is moulded to the stent scaffold and protrudes from within, in alignment with the stent pattern, while the inner permeable membrane remains in abutment with the inner circumference of the device. Hydrogels expand and cause the balloons to pop out.

FIGS. 7A-7D are perspective views of an impermeable sealing system to protect the implantable device during storage in a preservative solution such as glutaraldehyde, seals in place (FIG. 7A); exterior seal being removed (FIG. 7B); exterior seal removed and interior seals being removed (FIGS. 7C, 7D). FIG. 8 is a cross-sectional view of the exterior and interior seals of FIGS. 7A-7D.

As discussed above with reference to FIGS. 11A and 11B, self-aligning support members 82 made of Nitinol eliminate the use of attachment sutures within the catheter 80. The dual-membrane capsule containing the hydrogel can be attached to these members and is activated with the expansion of the prosthesis. The self-aligning members 82 can be directly laser-cut as part of the prosthesis frame 84 or can be connected using sutures. The primary advantage of this mechanism is that it eliminates any failure mode with the "activation member" (sutures, etc.) that enables the alignment of the capsule with the distal/proximal/middle section of the prosthesis. This embodiment allows placement of the device and sealing at the same time, and insures proper alignment of the device at the time of implantation.

As shown in FIGS. 12A-12F, the self-expanding TAV prosthesis frame 90 is released from the catheter 94 during deployment. Self-aligning support members 92 after release from the catheter "flip" and align themselves (and anything attached to it) to the base of the TAV prosthesis. The steps are followed in the reverse order during retrieval.

FIGS. 13A-13E show the deployment of a TAV device 110 using attachment sutures 112 that pull the seal 114 into place adjacent the device frame 116 at the time of implantation.

The seal may be sterile packaged for distribution and use. In the alternative, it may be packaged as part of, or in a kit with, the device it is designed to seal, such as a TAV or stent.

The present invention will be further understood by reference to the following non-limiting examples.

EXAMPLE 1

Preparation of Hydrogel with Rapid Swelling

Studies to identify hydrogels having substantial swelling in a short time were performed. The main factors that influence swelling of a hydrogel based on polymerisation and cross-linking of synthetic monomers are:
Type of monomer
Type of cross-linker
Concentration of monomer and cross-linker in the gel
The ratio of monomer to cross-linker
Acrylic acid polymers are capable of rapid swelling and are regarded as having good biocompatibility. A number of commercially available cross-linkers can be used to erosslink the polymers to form a hydrogel. These include Bis acrylamide, di(ethylene glycol)diacrylate, and poly(ethylene glycol)diacrylate (MW 500 Da).

Materials and Methods

Studies were conducted to identify appropriate combinations of acrylic acid concentration, type of cross-linker, concentration of cross-linker and ratio of monomer to cross-linker. The basic composition of the formulations used to make the gels is shown in Table 1. These were prepared as follows:

Mix acrylic acid with cross-linker and 50% of the necessary water, adjust pH to neutral with 15M sodium hydroxide and adjust the total volume with water.

Degas the solution under vacuum in a desiccator or other suitable container.

Add initiators (APS and TEMED), mix well and leave to gel overnight.

Test for mechanical properties and swelling.

After forming the gels in small beakers or Falcon tubes, the gels were cut into small pieces and dried until complete dryness. Small pieces of gel were then collected and re-swollen in phosphate buffered saline (PBS). The weight of the gel pieces were then recorded at regular intervals.

Results

Compositions and swelling data are shown in Tables 1 and 2.

TABLE 1

Swellable Formulations

| | Gel | | | | | | |
|---|---|---|---|---|---|---|---|
| | 2 | 3 | 5 | 6 | 21 | 29 | 25 |
| AA | 40 | 40 | 40 | 20 | 20 | 15 | 10 |
| Bis | 0.4 | 0.4 | 0.4 | 0.2 | 0.1 | 0.05 | 0.02 |

TABLE 1-continued

Swellable Formulations

| | | | | | | | |
|---|---|---|---|---|---|---|---|
| APS | 0.33 | 0.08 | 0.08 | 0.08 | 0.08 | 0.08 | 0.08 |
| TEMED | 0.33 | 0.8 | 0.08 | 0.08 | 0.1 | 0.1 | 0.1 |
| STATUS | Swelled | Swelled | Swelled | Swelled | Swelled | Swelled | Swelling |

| | Gel | | | | |
|---|---|---|---|---|---|
| | 17 | 23 | 19 | 26 | 28 |
| AA | 20 | 15 | 10 | 10 | 5 |
| PEG | 0.1 | 0.05 | 0.05 | 0.02 | 0.025 |
| APS | 0.08 | 0.08 | 0.08 | 0.08 | 0.08 |
| TEMED | 0.1 | 0.1 | 0.1 | 0.1 | 0.1 |
| STATUS | Swelled | Swelled | Swelled | Swelling | Swelling |

| | Gel | | |
|---|---|---|---|
| | 18 | 24 | 27 |
| AA | 20 | 15 | 10 |
| DEG | 0.1 | 0.05 | 0.02 |
| APS | 0.08 | 0.08 | 0.08 |
| TEMED | 0.1 | 0.1 | 0.1 |
| STATUS | Swelled | Swelled | Swelling |

TABLE 2

Analysis of Hydrogels made with the PVA cross-linker
DIMENSIONS AND SUMMARY

| Gel 23 rep 1 | | Gel 23 rep 2 | | Gel 23 rep 3 | |
|---|---|---|---|---|---|
| Approx. Shape | rectangular | Approx. Shape | triangle | Approx. Shape | rectangular |
| side 1 (mm) | 2 | base (mm) | 2 | side 1 (mm) | 1.5 |
| side 2 (mm) | 2 | height (mm) | 5 | side 2 (mm) | 1.25 |
| thickness (mm) | 0.33 | thickness (mm) | 0.25 | thickness (mm) | 0.625 |
| Volume (mm*3) | 3.333333333 | | 1.25 | | 1.171875 |
| Surface Area (mm *3) | 10.66666667 | | 12.8507 8106 10.2806 2485 | | 7.1875 6.133333333 |
| SA to V ratio | 8 | | | | |
| Beginning Mass (g) | 0.003 | | 0.003 | | 0.0009 0.00076 |
| Density (g/mm*) | 0.00225 | | 4.933333333 | | 8 8.666666467 |
| 5 min. swell ratio | 4.5 | | 3333 | | |

| Gel 23A rep 1 | | Gel 23A rep2 | | Gel 23A rep 3 | |
|---|---|---|---|---|---|
| Approx. Shape | triangle | Approx. Shape | trapezoid | Approx. Shape | trapezoid |
| side 1 (mm) | 2 | base 1 (mm) | 1 | base 1 (mm) | 1.5 |
| side 2 (mm) | 3 | base 2 (mm) | 1.5 | base 2 (mm) | 2 |
| thickness (mm) | 0.33 | height (mm) | 1 | height (mm) | 1 |
| height | | thickness | | thickness | |

TABLE 2-continued

Analysis of Hydrogels made with the PVA cross-linker
DIMENSIONS AND SUMMARY

| | rep 1 | rep 2 | rep 3 |
|---|---|---|---|
| (mm) thickness | | (mm) 0.25 | (mm) 0.585 |
| | 1 | 0.3125 | 1.02375 |
| | 8.77485 | 3.65450 | 6.78654 |
| | 1773 | 8497 | 9883 |
| | 8.77485 | 11.6344 | 6.62910 |
| | 1773 | 2719 | 8555 |
| | | 0.0008 | 0.0011 |
| | 0.0025 | | 0.001074481 |
| | | 0.00256 | |
| | 0.0025 | | 18.6363 |
| | 9.192307692 | 16.125 | 6364 |

| | Gel 23B rep 1 | Gel 23B rep 2 | Gel 23B rep 3 |
|---|---|---|---|
| Approx. Shape | triangle | Approx. Shape — | Approx. Shape — house |
| base (mm) | 4.5 | base (mm) 4 | bottom (mm) 1.5 |
| height (mm) | 5 | height (mm) 3 | side (mm) 2.5 |
| thickness (mm) | 1.49 | thickness (mm) 0.441 | triangle height (mm) 0.5 |
| | | | thickness (mm) 0.468 |
| Volume (mm*3) | 16.7625 | 2.646 | 1.9305 |
| Surface Area (mm 2) | 45.54412559 | 16.94409622 | 12.135699 |
| SA to V ratio | 2.717024644 | 6.403664484 | 6.286298367 |
| Beginning Mass (g) | 0.0177 | 0.0037 | 0.0015 |
| Density (g/mm*) | 0.001055928 | 0.003398337 | 0.000777001 |
| 5 min swell Ratio | 2.548022599 | 7.783783784 | 11.26666667 |

| | Gel 23C rep 1 | Gel 23C rep2 | Gel 23C rep 3 |
|---|---|---|---|
| Approx. Shape | square | Approx. Shape — triangle | Approx. Shape — rectangle |
| side 1 (mm) | 3 | base (mm) 3 | side 1 (mm) 1.5 |
| side 2 (mm) | 0.729 | height (mm) 3 | side 2 (mm) 2 |
| thickness (mm) | | thickness (mm) 0.448 | thickness (mm) 0.618 |
| | 6.561 | 2.016 | 1.854 |
| | | 13.34927536 | |
| | 26.748 | | 10.326 |
| | 4.07681 7558 | 6.621664366 | 5.569579288 |
| | | | 0.0014 |
| | 0.0034 | 0.002 | 0.00075 |
| | 0.000518214 | 0.000992063 | 5124 |
| | 9 | broke before 5 min | 10.07142857 |

Figure 14A:
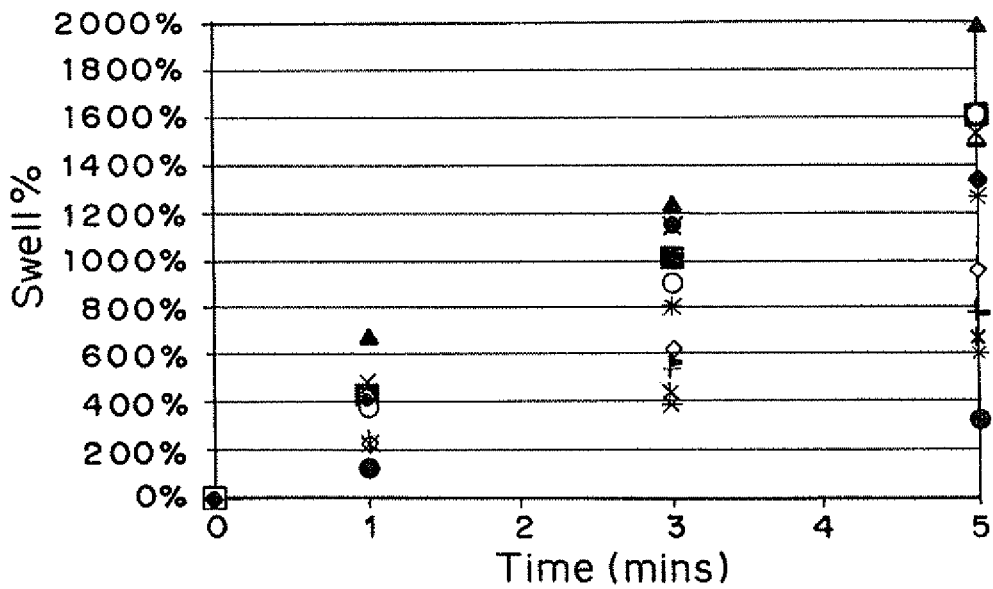
FIGS. 14A and 14B are graphs of percent swelling for the various formulations at 5 min (FIG. 14A) and 60 min (FIG. 14B).
Figure 14B:
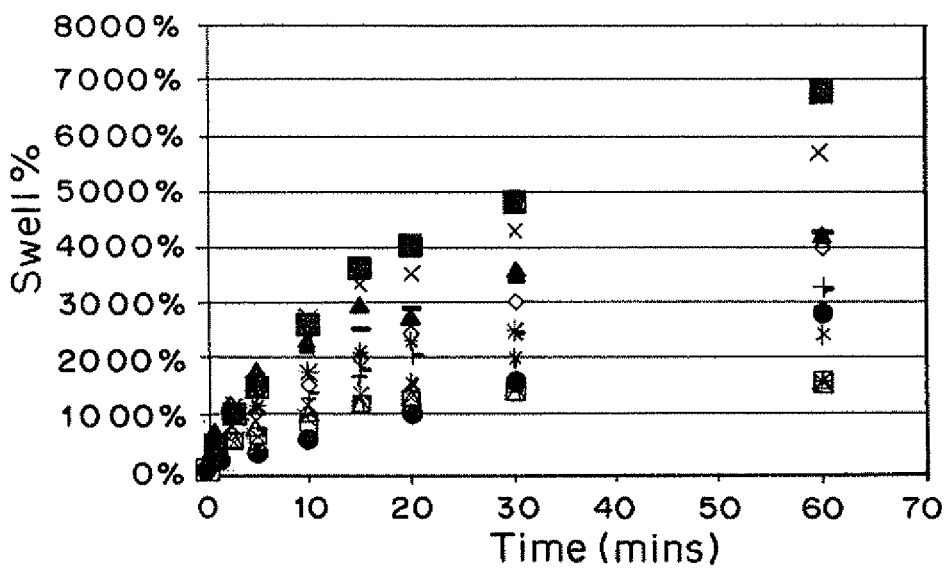

*for Gel 23 and Gel 23A rep 1 and 2, thickness is approximate, not measured with thickness gauge
ALL Gel 23 SAMPLES DISSLOVED AFTER A WHILE, PAST THE 3 MINUTE POINT Swelling data for the various formulations is graphed in FIG. 14A (swelling within 5 min) and FIG. 14B (swelling within 60 min).

As can be seen from the primary data, the quickest swelling gel was gel No. 23, which swelled 2000% in 5 min, which compares quite well to the 300% swelling rate for polyacrylamide gels. When allowed to swell for 60 min, gel No 19 swelled nearly 7000%, while gel No. 23 swelled 4000%.

As the ideal gel has rapid swelling and reaches its maximum swelling state quickly, gel No. 23 is the best gel based on swelling data alone. Gel No. 23 consists of 15% Acrylic acid and 0.05% poly(ethylene glycol)diacrylate.

Gel No. 19 consists of 10% Acrylic acid and 0.05% poly (ethylene glycol)diacrylate.

EXAMPLE 2

Assessment of Alternative Cross-Linkers for Hydrogels

The principle behind the selected cross-linkers is that rather than having a short cross-linker with only two polymerizable groups, a type of long-chain hydrophilic polymer with multiple polymerizable groups is being used. A much stronger hydrogel is obtained compared to short chain, divalent cross-linkers. While these gels are very firm, they possess very good swelling characteristics. Very strong gels do not normally swell very much.

Poly vinyl alcohol (PVA) was derivatized with allyl glycidyl ether under alkaline conditions. Gels were made by combing acrylic acid with the PVA-based cross-linker and then polymerizing the mixture by free radical polymerization using ammonium persulfate and TEMED as initiators.

The cross linker can be made with a number of different starting materials: A range of PVAs as well as partially hydrolyzed poly vinyl acetates, 2-hydroxyethyl methacrylates (HEMA) or various other polymers with reactive side groups can be used as the basic polymeric backbone. In addition, a wide range of natural hydrocolloids such as dextran, cellulose, agarose, starch, galactomannans, pectins, hyaluronic acid etc. can be used. A range of reagents such as allyl glycidyl ether, allyl bromide, allyl chloride etc. can be used to incorporate the necessary double bonds into this backbone. Depending on the chemistry employed, a number of other reagents can be used to incorporate reactive double bonds.

Materials and Methods

An alternative cross-linker, a multi-valent cross linker, was made by attaching allyl glycidyl ether to PVA (30-70 kDa). 2 g PVA was dissolved in 190 mL water; once fully dissolved, 10 mL 50% NaOH was added followed by 1 mL allyl glycidyl ether and 0.2 g sodium borohydride. Reaction was allowed to proceed for 16 hours followed by precipitation with isopropanol, washing of precipitate and redissolution in 50 mL of water. Efficiency of allyl group incorporation as well as concentration of concentration of re-dissolved cross-linker was not measured.

The components listed in Table 1 (excluding initiators) were mixed and degassed by placing the tubes in a desiccator with a vacuum applied. After 10 min the vacuum was turned off, and the tubes remained in the desiccator for a further 10 min under vacuum. The desiccator was opened and the initiators were added and the contents of the tubes mixed thoroughly. The tubes were capped and left overnight to cure.

Results

There was an increase in opacity of these gels from a to c. The gels also had a faint pink colour and the pH of the gelled material was 7.7. Swell rates for these gels are shown in Table 3.

Three gels containing 15% acrylic acid and cross linker in various concentrations were made and tested. The gels had gel strength that was significantly higher than the gels made with polyethylene glycol)diacrylate as cross linker. The gels had very good mechanical properties as well as very good swelling.

TABLE 3

Composition of gel Nos. 23 a-c

| component (mL) | Expt # | | |
| --- | --- | --- | --- |
| | 23a | 23b | 23c |
| acrylic acid | 1.5 | 1.5 | 1.5 |
| PVA cross-linker | 0.0526 | 0.526 | 5.26 |
| 50% NaOH | 1.251 | 2.15 | 2.35 |
| $H_2O$ | 7.122 | 5.779 | 0.795 |
| APS | 0.04 | 0.04 | 0.04 |
| TEMED | 0.05 | 0.05 | 0.05 |
| total | 10.02 | 10.05 | 10.00 |
| pH (pre-initiator addition) | 7.416 | 7.557 | 7.451 |

TABLE 4

Swell rates of gels made with PVA based cross-linker.

| Gel number | 23a | 23b | 23c |
| --- | --- | --- | --- |
| 5 min swelling* | 1000-2000% | 250-1100% | 900-1000% |
| 60 min swelling* | 4000-6000% | 1100-2500% | 3600-4300% |

*3 repeats were made for each gel swelling experiment

EXAMPLE 3

Demonstration of Sealing in In Vitro Model

Materials and Methods

Figures 15A, 15B:
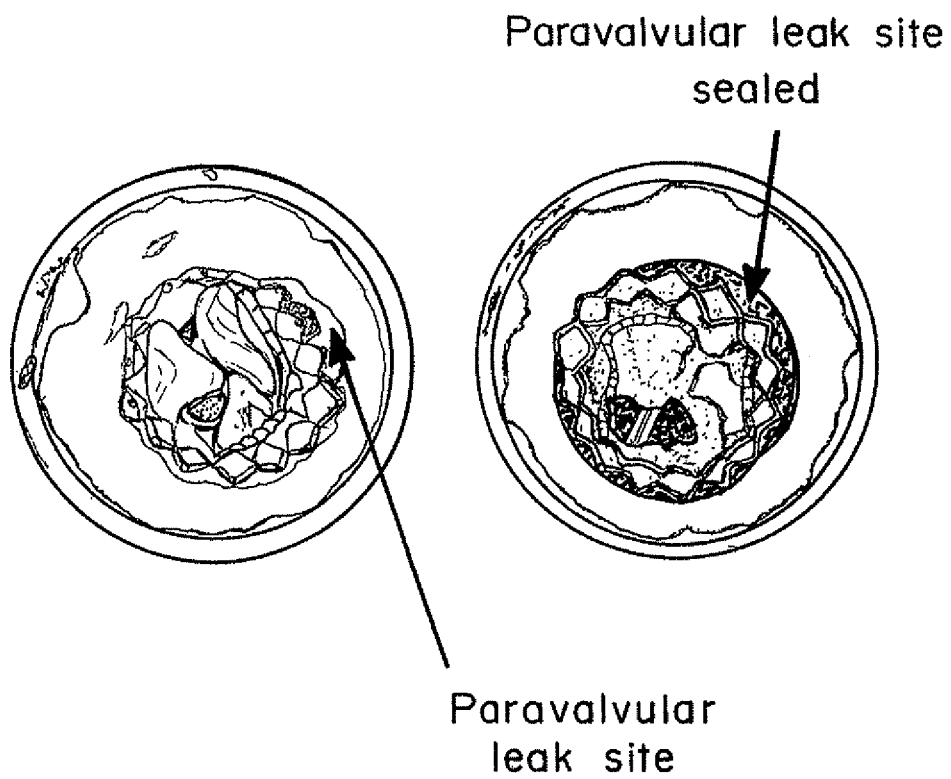
FIGS. 15A-15B show an in vitro model of a paravalvular leak site due to device inapposition (FIG. 15A) and the leak site sealed with the seal capsule without disturbing the base geometry of the device (FIG. 15B). The conformation of the seal happens actively only in places where there are leak sites. The seal does not decrease the central orifice area of the device not having any adverse effect on the blood flow as a result. View from heart into aorta; device of FIGS. 2A-2C.

An in vitro model of a TAV implantation shown in FIGS. 15A-15B was constructed using a tube having placed therein a TAV formed of a collapsible mesh 102 securing heart leaflets 104. In the model the mesh 102 did not seat uniformly into the tube, creating a paravalvular leak site 106 between a region of the mesh 102 and the tube 100.

The TAV includes an expandable seal as described above with reference to FIGS. 2A-2C. The seal 12 was expanded using wire 16 to expose seal 12 to the surrounding fluid (blood), causing the hydrogel to expand and press the seal 12 against the interior of the tube 100, causing the seal 12 membrane to seal the perivalvular leak site 108.

Results

FIG. 15A shows a paravalvular leak site 106 due to device inapposition. FIG. 15B shows the leak site is sealed with the seal capsule 108 without disturbing the base geometry of the device. The conformation of the seal happens actively only in places where there are leak sites. The seal does not decrease the central orifice area of the device not having any adverse effect on the blood flow as a result.

From the foregoing, it will be appreciated that specific embodiments of the disclosure have been described herein for purposes of illustration, but that various modifications may be made from these embodiments. Certain aspects of the disclosure described in the context of particular embodiments may be combined or eliminated in other embodiments. For example, a sealing device in accordance with particular embodiments may include only some of the foregoing components and features, and other devices may include other components and features in addition to those disclosed above. Further, while advantages associated with certain embodiments have been described in the context of those embodiments, other embodiments may also exhibit such advantages, and not all embodiments need necessarily exhibit such advantages. Accordingly, the disclosure can include other embodiments not shown or described above.

We claim:

1. An endoluminal seal for sealing an endoluminal implant or prosthesis to a wall of a lumen of a subject, the endoluminal seal comprising:
   an expandable material selected from the group consisting of hydrogels and foams,
   wherein the expandable material is expanded upon exposure to a fluid or a foaming agent,
   a semi-permeable first membrane adjacent to and encapsulating the expandable material,
   and
   an impermeable second membrane, metal foil or laminate preventing fluid or foaming agent from penetrating the semi-permeable first membrane to contact the expandable material prior to activation.

2. The endoluminal seal of claim 1 wherein the impermeable second membrane comprises a rupture site and activation means for rupturing the impermeable second membrane to allow fluid or foaming agent to penetrate the semi-permeable first membrane and contact the expandable material to expand the seal.

3. The endoluminal seal of claim 2 wherein the activation means is a wire connected to the rupture site that can be attached to the implant or prosthesis or aligned with a catheter element for placement of the implant or prosthetic.

4. The endoluminal seal of claim 2 further comprising an adhesive which is released when the rupture site is ruptured.

5. The endoluminal seal of claim 1 that is positioned within or is close abutment to the exterior of the implant or prosthesis, not changing the profile from that of the implant or prosthesis during implantation.

6. The endoluminal seal of claim 1 that expands under sufficient low pressure so that it seals the space between the implant or prosthesis and luminal wall, but does not push the implant or prosthesis away from the lumen wall.

7. The endoluminal seal of claim 1 wherein the seal actively conforms to a leak site between the lumen wall and the implant or prosthesis, without altering the rest of the device configuration.

8. The endoluminal seal of claim 1 wherein the first membrane has a pore size in the range of 50-70 microns.

9. The endoluminal seal of claim 1 wherein the expandable material is a hydrogel and the first membrane is permeable to fluid.

10. The endoluminal seal of claim 9 comprising a hydrogel material selected from the group consisting of polyacrylic acids and polyalkylene oxides.

11. The endoluminal seal of claim 1 comprising a support member which interfaces between the seal and the endoluminal implant or prosthesis and can go from an unexpanded or crimped state to an expanded state.

12. The endoluminal seal of claim 11 wherein the support member is an expandable mesh or struts, optionally including means for securing the implant or prosthesis at the site of implantation.

13. The endoluminal seal of claim 11 wherein the seal is crimped distal or proximal to the prosthesis, and aligned with the prosthesis prior to or at the time of placement.

14. The endoluminal seal of claim 1 wherein the activation means is an expansion means that increases pressure within the seal to rupture the impermeable second membrane.

15. The endoluminal seal of claim 1 further comprising a pharmaceutical, therapeutic or diagnostic agent to be released.

16. The endoluminal seal of claim 1 having a circumference complementary to a portion of the endoluminal implant or prosthesis, wherein the seal is in abutment to and substantially the same or less than the diameter of the endoluminal implant or prosthesis, prior to expansion of the seal.

17. The endoluminal seal of claim 1 for sealing of an endoluminal implant or prosthesis delivered in an introducer catheter or sheath, comprising an endoluminal implant or prosthesis and seal, wherein the seal is aligned with the endoluminal implant or prosthesis by expansion of the seal or the endoluminal implant or prosthesis.

18. The endoluminal seal of claim 1 for sealing of an endoluminal implant or prosthesis delivered in an introducer catheter or sheath, comprising an endoluminal implant or prosthesis and seal, wherein the seal is aligned with the region of the endoluminal implant or prosthesis to be sealed prior to expansion of the endoluminal implant or prosthesis by use of an activation member.

19. The endoluminal seal of claim 1 for sealing of an endoluminal implant or prosthesis in an introducer catheter, comprising an endoluminal implant or prosthesis and seal in the catheter within a fluid impermeable membrane, foil or laminate, wherein the seal is attached distal or proximal to the endoluminal implant or prosthesis, and aligns with a portion of the endoluminal implant or prosthesis when it is removed from the introducer catheter or sheath.

20. The endoluminal seal of claim 1 for sealing of endoluminal implant or prosthesis, comprising fixation members attaching the seal to a distal or proximal portion of the endoluminal implant or prosthesis, for delivery in an introducer catheter or sheath, wherein the fixation members pull the seal into abutment with a portion of the endoluminal implant or prosthesis when it is removed from the introducer catheter or sheath.

21. The endoluminal seal of claim 1 for sealing of endoluminal implant or prosthesis, comprising release members attaching the seal to a distal or proximal portion of the endoluminal implant or prosthesis, for recapture of the implant or prosthesis in an introducer catheter or sheath after complete or partial expansion, wherein the release members engage or disengage to enable the seal to be pulled into an introducer catheter or sheath.

22. A method of sealing a lumen comprising implanting an endoluminal implant or prosthetic comprising one or more of the endoluminal seal of claim 1 affixed thereto into a wall of a lumen of a subject.

23. The method of claim 22 comprising activating a rupture site of the endoluminal seal.

24. The method of claim 22 wherein the rupture site is activated by withdrawal of a wire attached thereto.

25. The method of claim 22 comprising attaching the endoluminal seal to a stent or valve prosthesis to form a sealable endoluminal device and inserting the endoluminal device into an insertional catheter with a guidewire.

26. The method of claim 22 further comprising releasing a therapeutic, prophylactic or diagnostic agent or adhesive at the site of sealing.

27. The method for implanting an endoluminal seal for sealing an endoluminal implant or prosthesis to a wall of a lumen of a subject of claim 22, the endoluminal seal comprising:
   an expandable material,
   semi-permeable first membrane adjacent to and containingencapsulating the expandable material;
   a removable impermeable second membrane preventing fluid from reaching the semi-permeable first membrane when the seal is stored in an aqueous environment,
   wherein the impermeable second membrane is removable by peeling, cracking, melting, or vaporization.

28. The seal of claim 27 wherein the impermeable second membrane is applied with plasma vapour deposition, vacuum deposition, co-extrusion, or press lamination.

* * * * *